US012612401B2

(12) United States Patent
Nuss et al.

(10) Patent No.: US 12,612,401 B2
(45) Date of Patent: Apr. 28, 2026

(54) CRYSTALLINE FORMS OF AN S1P RECEPTOR MODULATOR

(71) Applicant: Oppilan Pharma Limited, Encinitas, CA (US)

(72) Inventors: John Nuss, Encinitas, CA (US); Jason Harris, Encinitas, CA (US); Shendong Yuan, Encinitas, CA (US); Scott Alan Wolckenhauer, Encinitas, CA (US)

(73) Assignee: OPPILAN PHARMA LIMITED, London (GB)

( * ) Notice: Subject to any disclaimer, the term of this patent is extended or adjusted under 35 U.S.C. 154(b) by 417 days.

(21) Appl. No.: 18/347,491

(22) Filed: Jul. 5, 2023

(65) Prior Publication Data

US 2024/0010649 A1 Jan. 11, 2024

Related U.S. Application Data

(60) Provisional application No. 63/358,791, filed on Jul. 6, 2022.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................... C07D 471/04
USPC .......................................................... 514/300
See application file for complete search history.

(56) References Cited

U.S. PATENT DOCUMENTS

| | | | |
|---|---|---|---|
| 4,327,725 | A | 5/1982 | Cortese et al. |
| 4,624,848 | A | 11/1986 | Lee |
| 4,968,509 | A | 11/1990 | Radebaugh et al. |
| 5,323,907 | A | 6/1994 | Kalvelage |
| 5,456,923 | A | 10/1995 | Nakamichi et al. |
| 5,461,140 | A | 10/1995 | Heller et al. |
| 5,516,527 | A | 5/1996 | Curatolo |
| 5,622,721 | A | 4/1997 | Dansereau et al. |
| 5,686,105 | A | 11/1997 | Kelm et al. |
| 5,700,410 | A | 12/1997 | Nakamichi et al. |
| 5,977,175 | A | 11/1999 | Lin |
| 6,465,014 | B1 | 10/2002 | Moroni et al. |
| 6,932,983 | B1 | 8/2005 | Straub et al. |
| 7,834,039 | B2 | 11/2010 | Hobson et al. |
| 10,683,291 | B2 | 6/2020 | Mohan et al. |
| 2007/0043014 | A1 | 2/2007 | Doherty et al. |
| 2009/0176778 | A1* | 7/2009 | Schmitz .................... A61P 1/16 514/233.2 |
| 2010/0160369 | A1 | 6/2010 | Canne Bannen et al. |
| 2011/0071570 | A1 | 3/2011 | Trieu |
| 2011/0207704 | A1 | 8/2011 | Cusack et al. |
| 2013/0158001 | A1 | 6/2013 | Das et al. |
| 2013/0196966 | A1 | 8/2013 | Martinborough et al. |
| 2020/0325135 | A1 | 10/2020 | Mohan et al. |
| 2022/0227767 | A1 | 7/2022 | Mohan et al. |
| 2023/0339944 | A1 | 10/2023 | Mohan et al. |

FOREIGN PATENT DOCUMENTS

| | | | |
|---|---|---|---|
| EP | 0138539 | A1 | 4/1985 |
| WO | WO-2005032465 | A2 | 4/2005 |
| WO | WO-2006011336 | A1 | 2/2006 |
| WO | WO-2006131336 | A1 | 12/2006 |
| WO | WO-2008076356 | A1 | 6/2008 |
| WO | WO-2010065760 | A1 | 6/2010 |
| WO | WO-2010117662 | A1 | 10/2010 |
| WO | WO-2011071570 | A1 | 6/2011 |
| WO | WO-2013059594 | A1 | 4/2013 |
| WO | WO-2015078374 | A1 | 6/2015 |
| WO | WO-2017083756 | A1 | 5/2017 |
| WO | WO-2018211324 | A1 | 11/2018 |
| WO | WO-2024011142 | A1 | 1/2024 |
| WO | WO-2024151993 | A1 | 7/2024 |

OTHER PUBLICATIONS

Bamias et al. Targeting S1P Receptors, A New Mechanism of Action for Inflammatory Bowel Disease Therapy. Gastroenterology 151(5):1025-1027 (2017).
Berge et al. Pharmaceutical Salts. Journal of Pharmaceutical Sciences 66(1):1-19 (Jan. 1977).
Bernstein. Crystal Structure Prediction and Polymorphism. ACA Transactions 39:14-23 (2004).
Braga et al. Making crystals from crystals: a green route to crystal engineering and polymorphism. J. Royal Soc. Chem. Commun 29:3635-3645 (2005).
Bundgaard. Design and Application of Prodrugs. Textbook of Drug Design and Development. Krosgaard-Larsen and Bundgaard. Chapter 5. pp. 113-191 (1991).
Bundgaard. Means to Enhance Penetration: Prodrugs as a Means to Improve the Delivery of Peptide Drugs. Advanced Drug Delivery Review 8:1-38 (1992).
International Conference on Harmonization of Technical Requirements for Registration of Pharmaceuticals for Human Use (ICH), "Impurities: Guidelines for Residual Solvents Q3C(R6)." (Oct. 2016).
Jones et al. Pharmaceutical Cocrystals: An Emerging Approach to Physical Property Enhancement. MRS Bulletin 31:875-879 (2006).
Liberman et al. Pharmaceutical Dosage Forms. 2nd Ed. 1:209-214 (1990).
PCT/US2016/061676 International Search Report and Written Opinion dated Jan. 5, 2017.
Price. The computational prediction of pharmaceutical crystal structures and polymorphism. Advanced Drug Delivery Reviews 56:301-319 (2004).
Rosen et al. Sphingosine 1-phosphate receptor signaling. Annu Rev Biochem 78:743-68 (2009).
Science IP Report (4 pgs.) (2016).
Science IP Report (63 pgs.) (2016).

(Continued)

*Primary Examiner* — Niloofar Rahmani
(74) *Attorney, Agent, or Firm* — WILSON SONSINI GOODRICH & ROSATI

(57) ABSTRACT

Described herein are crystalline forms of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or a salt or solvate thereof.

20 Claims, 9 Drawing Sheets

(56) References Cited

OTHER PUBLICATIONS

Shah et al. The role of fluorine in medicinal chemistry. Journal of Enzyme Inhibition and Medicinal Chemistry 22(5):527-540 (Oct. 2007).
Silverman. The Organic Chemistry of Drug Design and Drug Action, published 1992 by Academic Press, p. 19.
Singh et al. Encyclopedia of Pharmaceutical Technology 2nd Ed. pp. 751-753 (2002).
Tully et al. 2-(oxadiazolyl)- and 2-(thiazolyl)imidazo[1,2-a]pyrimidines as agonists and inverse agonists at benzodiazepine receptors. J Med Chem 34:2060-2067 (1991).
U.S. Appl. No. 15/775,723 Office Action dated Sep. 12, 2019.
U.S. Appl. No. 16/865,212 Office Action dated Sep. 20, 2021.
Widder et al. Section III: Prodrugs Kinetics. Method in Enzymology. 112:309-396 (1985).
Caira. Crystalline Polymorphism of Organic Compounds. Topics in Current Chemistry. 198:163-208 (Jan. 1998).
PCT/US2023/069659 International Search Report and Written Opinion dated Sep. 27, 2023.
Saal et al. Pharmaceutical salts: a summary on doses of salt formers from the Orange Book. Eu J Pharm 49(4):614-623 (2013).
Unknown. The Complete Blog for the Preparation of Pharmaceutical Salts. (10 pgs) (2008). Retrieved from the Internet: http://kilomentor.chemicalblogs.com/55_kilomentor/archive/552_the_complete_blog_for_the_preparation_of_pharmaceutical_salts.html [retrieved on Feb. 4, 2009].

* cited by examiner

CRYSTALLINE FORMS OF AN S1P RECEPTOR MODULATOR

CROSS-REFERENCE

This application claims benefit of U.S. Provisional Patent Application No. 63/358,791, filed on Jul. 6, 2022, which is incorporated herein by reference in its entirety.

BACKGROUND

The sphingosine-1-phosphate (SiP) receptors are a class of G protein-coupled receptors that are targets of the lipid signaling molecule sphingosine-1-phosphate. Sphingosine-1-phosphate (SiP) is a bioactive sphingolipid that has been demonstrated to induce many cellular processes, including those that result in platelet aggregation, cell proliferation, cell morphology, tumor-cell invasion, endothelial cell chemotaxis and angiogenesis, cytoskeletal re-arrangements in many cell types to regulate immune cell trafficking, vascular homeostasis and cell communication in the central nervous system (CNS) and in peripheral organ systems. SiP can bind with members of the endothelial cell differentiation gene family (EDG receptors) of plasma membrane-localized G protein-coupled receptors. To date, five members of this family have been identified as SiP receptors in different cell types, S1P1 (EDG-1), S1P2 (EDG-5), S1P3 (EDG-3), S1P4 (EDG-6) and S1P5 (EDG-8). SiP receptor modulators are compounds which signal as agonists or antagonists at one or more SiP receptors. Since SiP mediates a wide variety of cellular responses, SiP receptor modulators are promising targets for a variety of therapeutic indications.

SUMMARY OF THE INVENTION

In one aspect, described herein is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or a salt or solvate thereof.

In some embodiments, the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 1 having at least one of the following properties:

(a) an X-ray powder diffraction (XRPD) pattern substantially the same as shown in FIG. 1;

(b) an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta;

(c) a thermo-gravimetric analysis (TGA) substantially similar to the one set forth in FIG. 2;

(d) a DSC thermogram substantially similar to the one set forth in FIG. 2;

(e) a DSC thermogram with an endotherm having an onset at about 282° C.; or (f) combinations thereof.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern substantially the same as shown in FIG. 1.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a thermogravimetric analysis (TGA) substantially similar to the one set forth in FIG. 2.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram substantially similar to the one set forth in FIG. 2.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram with an endotherm having an onset at about 282° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is characterized as having properties: (a) an X-ray powder diffraction (XRPD) pattern substantially the same as shown in FIG. 1; (b) an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta; (c) a thermo-gravimetric analysis (TGA) substantially similar to the one set forth in FIG. 2; (d) a DSC thermogram substantially similar to the one set forth in FIG. 2; and (e) a DSC thermogram with an endotherm having an onset at about 282° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is obtained from THE or EtOAc.

In some embodiments, crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is unsolvated.

In another embodiment, is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 2 having at least one of the following properties:

(a) an X-ray powder diffraction (XRPD) pattern substantially the same as shown in FIG. 3;

(b) an X-ray powder diffraction (XRPD) pattern with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta;

(c) a thermo-gravimetric analysis (TGA) substantially similar to the one set forth in FIG. 4;

(d) a DSC thermogram substantially similar to the one set forth in FIG. 4;

(e) a DSC thermogram with a first endotherm having an onset at about 145° C. and a second endotherm having an onset at about 180° C.; or (f) combinations thereof.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern substantially the same as shown in FIG. 3.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a thermogravimetric analysis (TGA) substantially similar to the one set forth in FIG. 4.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram substantially similar to the one set forth in FIG. 4.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram with a first endotherm having an onset at about 145° C. and a second endotherm having an onset at about 280° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is characterized as having properties: (a) an X-ray powder diffraction (XRPD) pattern substantially the same as shown in FIG. 3; (b) an X-ray powder diffraction (XRPD) pattern with characteristic peaks at 7.0° 2-Theta, 9.5° 2-Theta, 11.2° 2-Theta, 14.9° 2-Theta, 18.6° 2-Theta, 22.1° 2-Theta, 24.1° 2-Theta, 26.2° 2-Theta, and 30.0° 2-Theta; (c) a thermogravimetric analysis (TGA) substantially similar to the one set forth in FIG. 4; (d) a DSC thermogram substantially similar to the one set forth in FIG. 4; (e) a DSC thermogram with a first endotherm having an onset at about 145° C. and a second endotherm having an onset at about 280° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is obtained from acetic acid.

In some embodiments, crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is a acetic acid solvate.

In another embodiment, is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, wherein the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate is Form 3 having at least one of the following properties:

(a) an X-ray powder diffraction (XRPD) pattern substantially the same as shown in FIG. 5;

(b) an X-ray powder diffraction (XRPD) pattern with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta;

(c) a thermo-gravimetric analysis (TGA) substantially similar to the one set forth in FIG. 6;

(d) a DSC thermogram substantially similar to the one set forth in FIG. 6;

(e) a DSC thermogram with a first endotherm at about 41° C., a second endotherm having an onset at about 93° C., and a third endotherm having an onset at about 156° C.; or (f) combinations thereof.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern substantially the same as shown in FIG. 5.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a thermogravimetric analysis (TGA) substantially similar to the one set forth in FIG. 6.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram substantially similar to the one set forth in FIG. 6.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram with a first endotherm at about 41° C., a second endotherm having an onset at about 93° C., and a third endotherm having an onset at about 156° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is characterized as having properties: (a) an X-ray powder diffraction (XRPD) pattern substantially the same as shown in FIG. 5; (b) an X-ray powder diffraction (XRPD) pattern with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta; (c) a thermogravimetric analysis (TGA) substantially similar to the one set forth in FIG. 6; (d) a DSC thermogram substantially similar to the one set forth in FIG. 6; and (e) a DSC thermogram with a first endotherm at about 41° C., a second endotherm having an onset at about 93° C., and a third endotherm having an onset at about 156° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is obtained from ethyl acetate.

In another embodiment, is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, wherein the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate is Form 4 having at least one of the following properties:

(a) an X-ray powder diffraction (XRPD) pattern substantially the same as shown in FIG. 7;

(b) an X-ray powder diffraction (XRPD) pattern with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta;

(c) a thermo-gravimetric analysis (TGA) substantially similar to the one set forth in FIG. 8;

(d) a DSC thermogram substantially similar to the one set forth in FIG. 8;

(e) a DSC thermogram with a first endotherm at about 60° C. and a second endotherm having an onset at about 128° C.; or (f) combinations thereof.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern substantially the same as shown in FIG. 7.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has an X-ray powder diffraction (XRPD) pattern with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a thermogravimetric analysis (TGA) substantially similar to the one set forth in FIG. 8.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram substantially similar to the one set forth in FIG. 8.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form has a DSC thermogram with a first endotherm at about 60° C. and a second endotherm having an onset at about 128° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is characterized as having properties: (a) an X-ray powder diffraction (XRPD) pattern substantially the same as shown in FIG. 7; (b) an X-ray powder diffraction (XRPD) pattern with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta; (c) a thermogravimetric analysis (TGA) substantially similar to the one set forth in FIG. 8; (d) a DSC thermogram substantially similar to the one set forth in FIG. 8; and (e) a DSC thermogram with a first endotherm at about 60° C. and a second endotherm having an onset at about 128° C.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, wherein the crystalline form is obtained from ethyl acetate.

In some embodiments is a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, for use in medicine.

In some embodiments is (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, wherein (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is amorphous.

In another aspect, described herein is a pharmaceutical composition comprising a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, and a pharmaceutically acceptable excipient.

In another aspect, described herein is a pharmaceutical composition comprising a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, formulated for oral, intravenous, intramuscular, or subcutaneous administration.

In another aspect, described herein is a method of treating a disease, disorder or condition in a mammal that would benefit from sphingosine-1-phosphate (SiP) receptor modulation, comprising administering to the individual a therapeutically effective amount of a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof.

In some embodiments is a method for treating a disease in a mammal is selected from multiple sclerosis, ulcerative colitis, and Crohn's disease.

In some embodiments is a method for treating a disease in an individual in need thereof, comprising administering to the individual a therapeutically effective amount of a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, described herein, wherein (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is administered orally. In some embodiments is a method for treating immune disorder in an individual in need thereof, comprising administering to the individual a therapeutically effective amount of a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, described herein, wherein the therapeutically effective amount is taken with food. In some embodiments is a method for treating immune disorder in an individual in need thereof, comprising administering to the individual a therapeutically effective amount of a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, described herein, wherein the therapeutically effective amount is taken without food. In some embodiments is a method for treating immune disorder in an individual in need thereof, comprising administering to the individual a therapeutically effective amount of a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, described herein, wherein (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is administered to the individual once per day. In some embodiments is a method for treating immune disorder in an individual in need thereof, comprising administering to the individual a therapeutically effective amount of a crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, or solvate thereof, described herein, wherein (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is administered to the individual twice per day.

INCORPORATION BY REFERENCE

All publications, patents, and patent applications mentioned in this specification are herein incorporated by reference to the extent applicable and relevant and to the same extent as if each individual publication, patent, or patent application was specifically and individually indicated to be incorporated by reference.

DETAILED DESCRIPTION OF THE INVENTION

Figure 1:
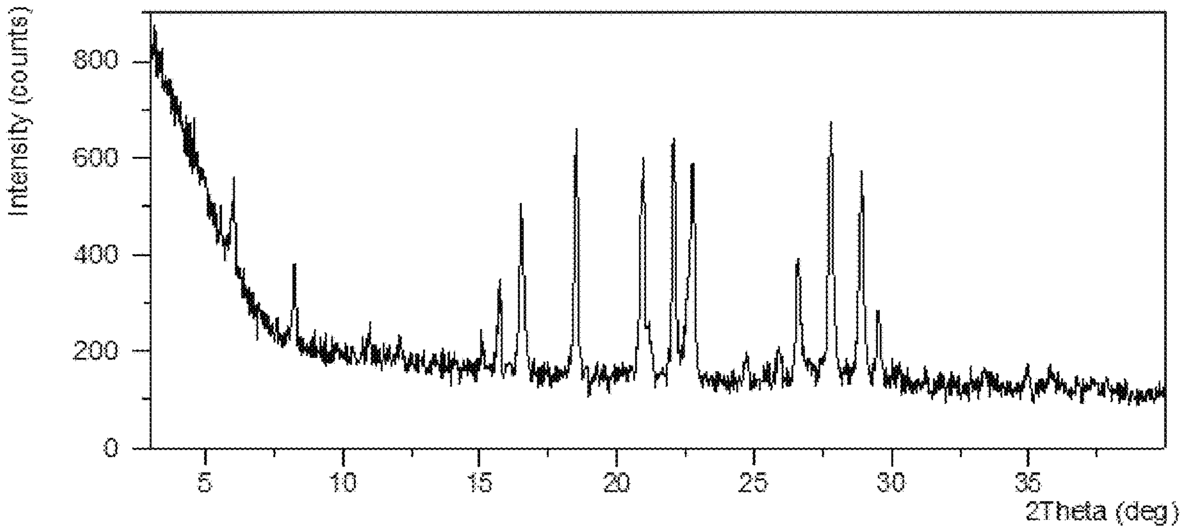
FIG. 1. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 1.

The sphingosine-1-phosphate receptors regulate fundamental biological processes such as cell proliferation, angiogenesis, migration, cytoskeleton organization, endothelial cell chemotaxis, immune cell trafficking and mitogenesis. Sphingosine-1-phosphate receptors are also involved in immune-modulation and directly involved in suppression of innate immune responses from T cells. Sphingosine-1-phosphate (SiP) receptors are divided into five subtypes: S1PR1, S1PR2, S1PR3, S1PR4 and S1PR5. They are expressed in a wide variety of tissues, with each subtype exhibiting different cell specificity, although they are found at their highest density on leukocytes.

In one aspect is the administration of at least one SiP receptor modulator described herein to a mammal in the treatment of diseases, disorders or conditions that would benefit from SiP receptor modulation. In some aspects is the administration of at least one SiP receptor modulator described herein to a mammal in the treatment of diseases, disorders or conditions that would benefit from the selective modulation of SiP receptor subtypes. In some embodiments is the administration of at least one SiP receptor modulator described herein to a mammal in the treatment of diseases, disorders or conditions that would benefit from the selective modulation of two SiP receptor subtypes. In some embodiments is the administration of at least one SiP receptor modulator described herein to a mammal in the treatment of diseases, disorders or conditions that would benefit from the selective modulation of one SiP receptor subtype.

Compound 1

In one embodiment is (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one. "Compound 1" or "(R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one" refers to the compound with the following structure:

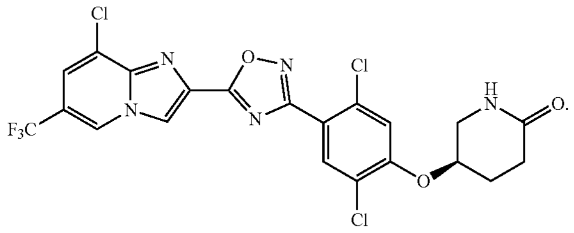 [SMILES: O=C1CC[C@@H](Oc2cc(Cl)c(-c3noc(-c4cn5cc(C(F)(F)F)cc(Cl)c5n4)n3)cc2Cl)CN1]

In some embodiments described herein are pharmaceutically acceptable salts of Compound 1. The term "pharmaceutically acceptable salts" in reference to Compound 1 refers to a salt of Compound 1, which does not cause significant irritation to a mammal to which it is administered and does not substantially abrogate the biological activity and properties of the compound. In some embodiments a pharmaceutically acceptable salt includes:

- acid addition salts formed by reacting Compound 1 with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, adipic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, benzenesulfonic acid, p-toluenesulfonic acid, salicylic acid, and the like;
- acid addition salts formed by reacting Compound 1 with an inorganic acid, which includes hydrochloric acid, hydrobromic acid, sulfuric acid, nitric acid, phosphoric acid, hydroiodic acid, hydrofluoric acid, phosphorous acid, and the like.

In some embodiments, (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one includes the solvent addition forms (solvates). Solvates contain either stoichiometric or non-stoichiometric amounts of a solvent, and are formed during the process of product formation or isolation with pharmaceutically acceptable solvents such as water, ethanol, methanol, tert-butyl methyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In some embodiments, solvates are formed using, but not limited to, Class 3 solvent(s). In some embodiments, solvates are formed using, but not limited to, Class 2 solvent(s). Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016). Hydrates are formed when the solvent is water, or alcoholates are formed when the solvent is alcohol.

In other embodiments, (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is prepared in various forms, including but not limited to, an amorphous phase, crystalline forms, milled forms, and nano-particulate forms. In some embodiments, Compound 1, or a pharmaceutically acceptable salt thereof, is amorphous and anhydrous. In some embodiments, Compound 1, or a pharmaceutically acceptable salt thereof, is crystalline. In some embodiments, Compound 1, or a pharmaceutically acceptable salt thereof, is crystalline and anhydrous.

While not intending to be bound by any particular theory, certain solid forms are characterized by physical properties, e.g., stability, solubility, and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein.

Crystalline Forms

The identification and selection of a solid form of a pharmaceutical compound are complex, given that a change in solid form may affect a variety of physical and chemical properties, which may provide benefits or drawbacks in processing, formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict apriori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable, and marketable pharmaceutical product.

Crystalline Compound 1, Form 1

Figure 2:
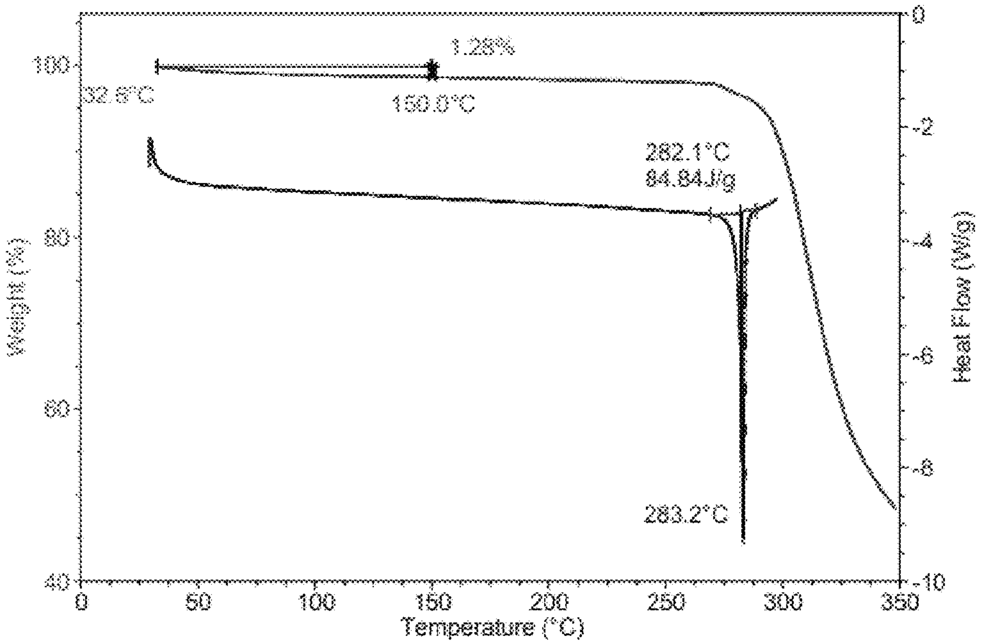
FIG. 2. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 1.

In some embodiments, (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is crystalline. In some embodiments, (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is crystalline and anhydrous. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 1 characterized as having at least one of the following properties:

(a) an X-ray powder diffraction (XRPD) pattern substantially the same as shown in FIG. 1;

(b) an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta;

(c) a thermogravimetric analysis (TGA) substantially similar to the one set forth in FIG. 2;

(d) a DSC thermogram substantially similar to the one set forth in FIG. 2;

(e) a DSC thermogram with an endotherm having an onset at about 282° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, has an X-ray powder diffraction (XRPD) pattern substantially the same as shown in FIG. 1. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, has an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, has a thermogravimetric analysis (TGA) thermogram substantially similar to the one set forth in FIG. 2. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, has a DSC thermogram substantially similar to the one set forth in FIG. 2. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, has a DSC thermogram with an endotherm having an onset at about 282° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is obtained from THE or ethyl acetate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is obtained from ethyl acetate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is obtained from THF. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 1, is unsolvated.

Crystalline Compound 1, Form 2

Figure 3:
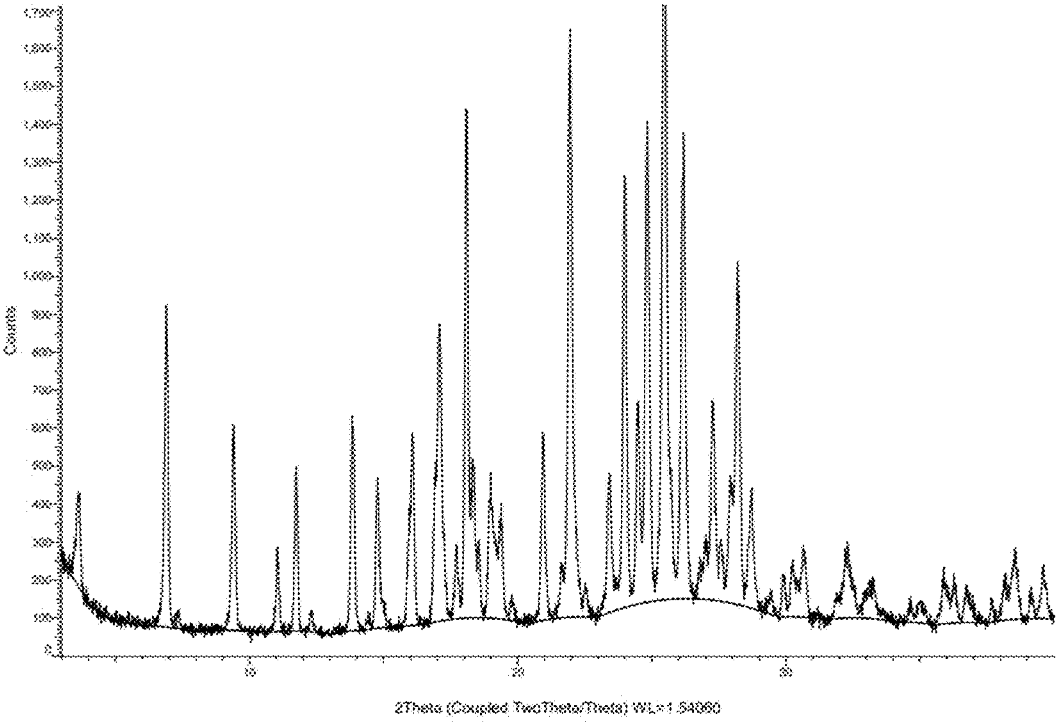
FIG. 3. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 2.
Figure 4:
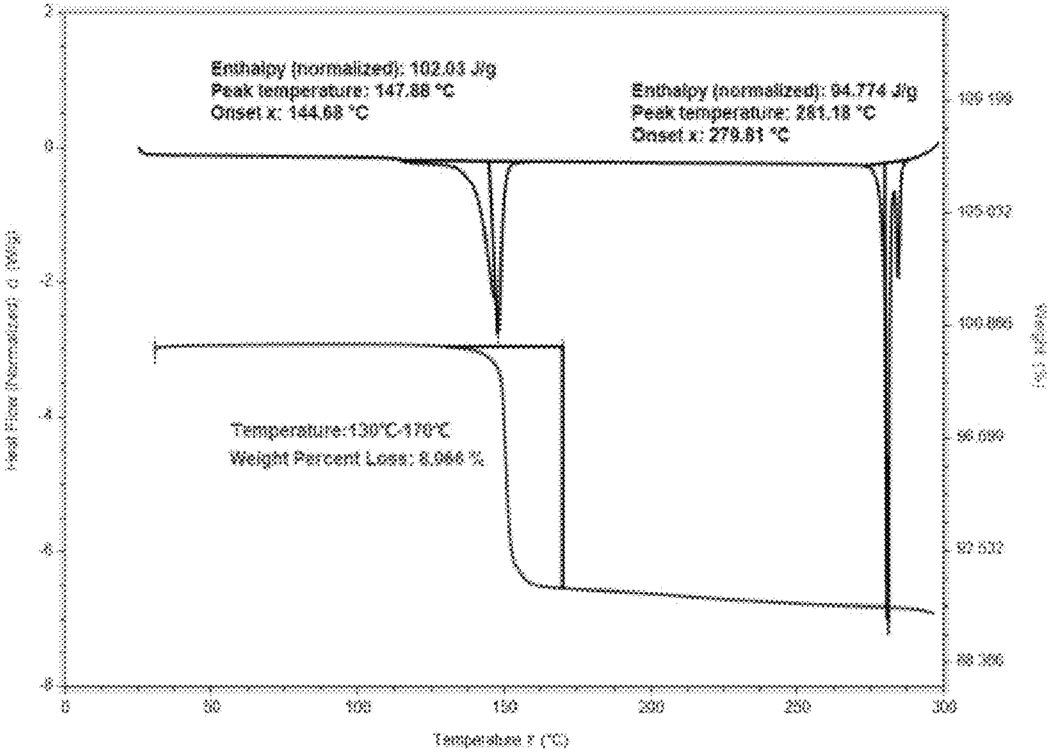
FIG. 4. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 2.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 2 characterized as having at least one of the following properties:

(a) an X-ray powder diffraction (XRPD) pattern substantially the same as shown in FIG. 3;

(b) an X-ray powder diffraction (XRPD) pattern with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta;

(c) a thermogravimetric analysis (TGA) substantially similar to the one set forth in FIG. 4;

(d) a DSC thermogram substantially similar to the one set forth in FIG. 4;

(e) a DSC thermogram with a first endotherm having an onset at about 145° C. and a second endotherm having an onset at about 280° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, has an X-ray powder diffraction (XRPD) pattern substantially the same as shown in FIG. 3. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, has an X-ray powder diffraction (XRPD) pattern with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, has a thermogravimetric analysis (TGA) thermogram substantially similar to the one set forth in FIG. 4. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, has a DSC thermogram substantially similar to the one set forth in FIG. 4. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, has a DSC thermogram with a first endotherm having an onset at about 145° C. and a second endotherm having an onset at about 280° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is obtained from acetic acid. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is an acetic acid solvate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 2, is unsolvated.

Crystalline Compound 1 Tosylate, Form 3

Figure 5:
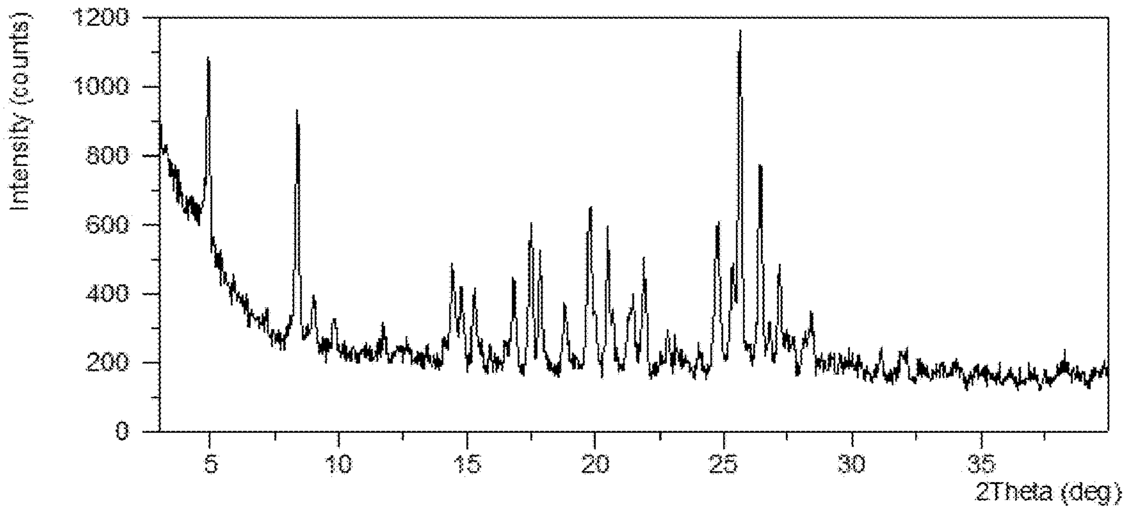
FIG. 5. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1) tosylate, Form 3.
Figure 6:
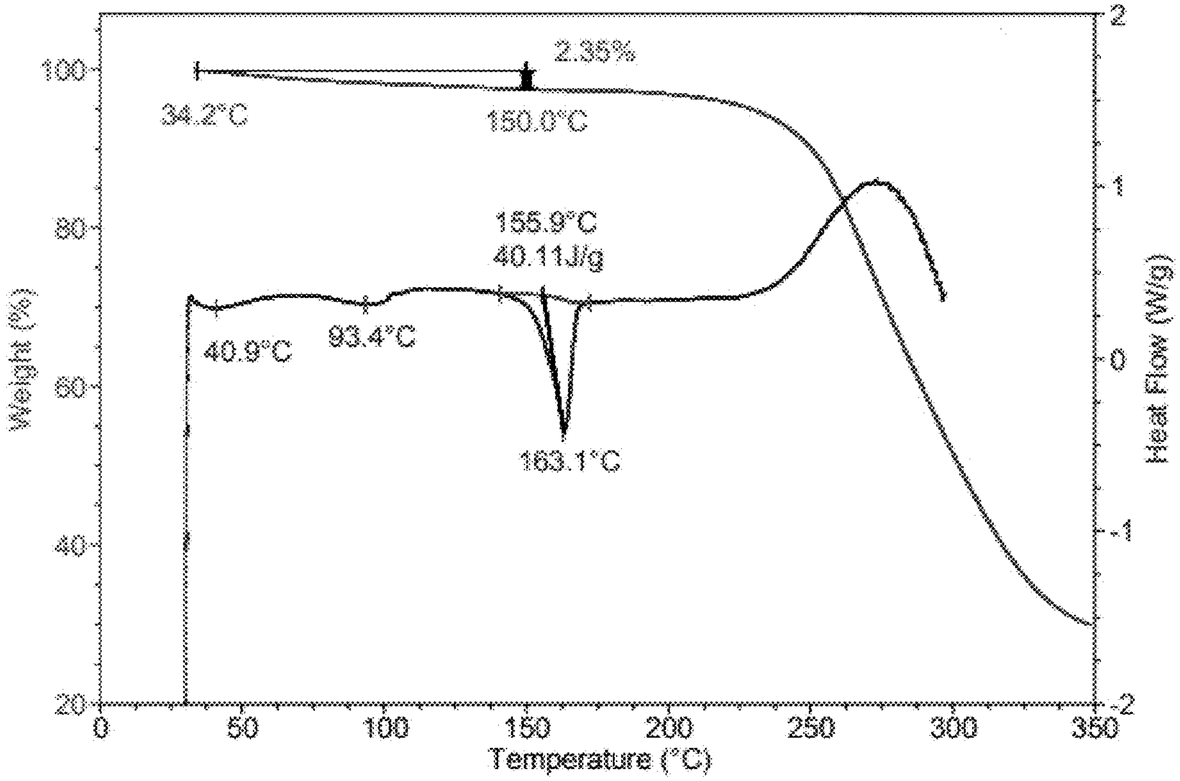
FIG. 6. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1) tosylate, Form 3.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is a para-toluenesulfonic acid salt and the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate is Form 3 having at least one of the following properties:

(a) an X-ray powder diffraction (XRPD) pattern substantially the same as shown in FIG. 5;

(b) an X-ray powder diffraction (XRPD) pattern with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta;

(c) a thermogravimetric analysis (TGA) substantially similar to the one set forth in FIG. 6;

(d) a DSC thermogram substantially similar to the one set forth in FIG. 6;

(e) a DSC thermogram with a first endotherm at about 41° C., a second endotherm having an onset at about 93° C., and a third endotherm having an onset at about 156° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, has an X-ray powder diffraction (XRPD) pattern substantially the same as shown in FIG. 5. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, has an X-ray powder diffraction (XRPD) pattern with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, has a thermogravimetric analysis (TGA) thermogram substantially similar to the one set forth in FIG. 6. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, has a DSC thermogram substantially similar to the one set forth in FIG. 6. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, has a DSC thermogram with a first endotherm at about 41° C., a second endotherm having an onset at about 93° C., and a third endotherm having an onset at about 156° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is obtained from ethyl acetate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one tosylate, Form 3, is unsolvated.

Crystalline Compound 1 Mesylate, Form 4

Figure 7:
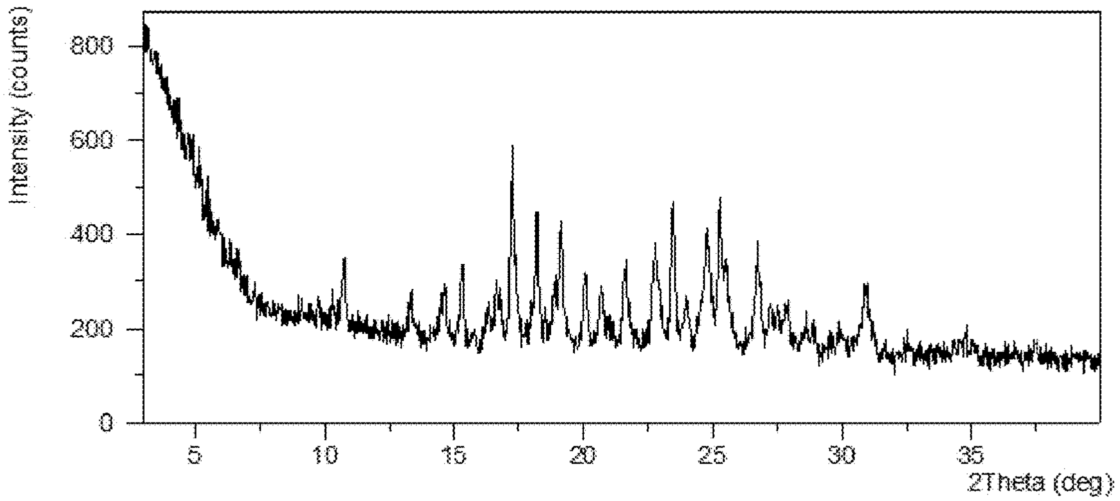
FIG. 7. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1) mesylate, Form 4.
Figure 8:
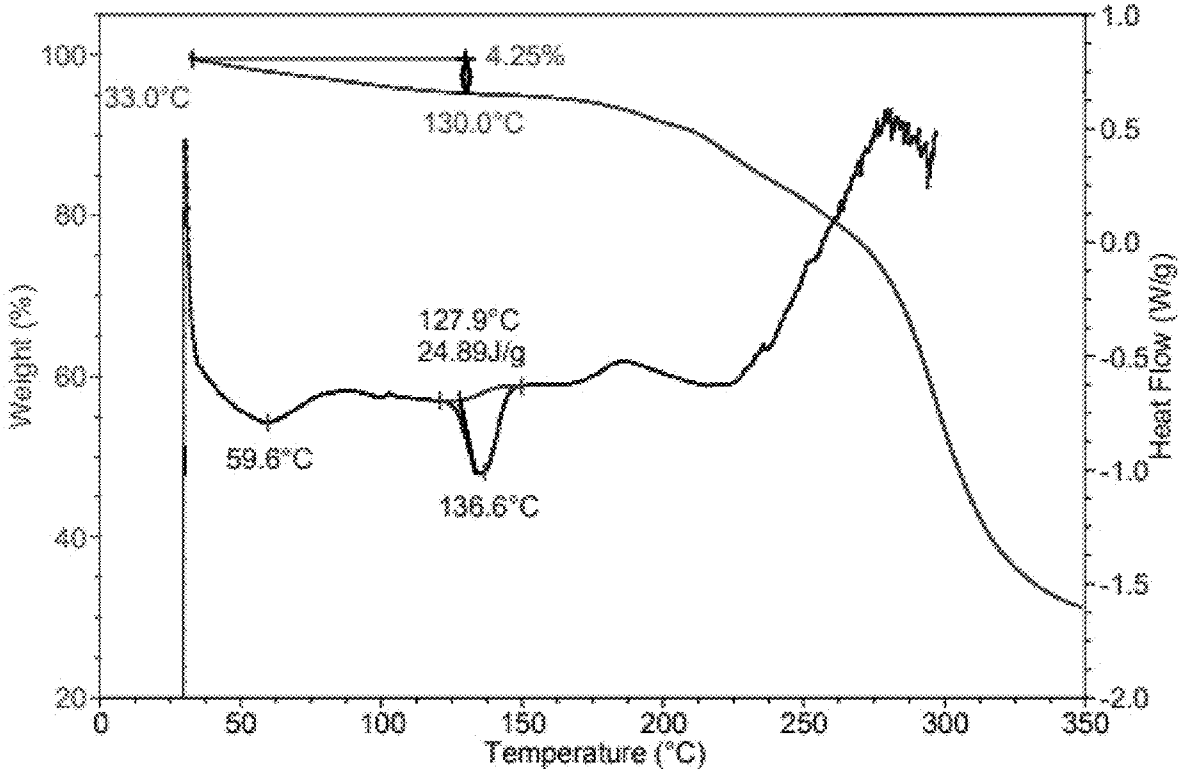
FIG. 8. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1) mesylate, Form 4.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is a methanesulfonic acid salt and the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate is Form 4 having at least one of the following properties:

(a) an X-ray powder diffraction (XRPD) pattern substantially the same as shown in FIG. 7;

(b) an X-ray powder diffraction (XRPD) pattern with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta;

(c) a thermogravimetric analysis (TGA) substantially similar to the one set forth in FIG. 8;

(d) a DSC thermogram substantially similar to the one set forth in FIG. 8;

(e) a DSC thermogram with a first endotherm at about 60° C. and a second endotherm having an onset at about 128° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, has an X-ray powder diffraction (XRPD) pattern substantially the same as shown in FIG. 7. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, has an X-ray powder diffraction (XRPD) pattern with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, has a thermogravimetric analysis (TGA) thermogram substantially similar to the one set forth in FIG. 8. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, has a DSC thermogram substantially similar to the one set forth in FIG. 8. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, has a DSC thermogram with a first endotherm at about 60° C. and a second endotherm having an onset at about 128° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is obtained from ethyl acetate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one mesylate, Form 4, is unsolvated.

Crystalline Compound 1, Form 5

Figure 9:
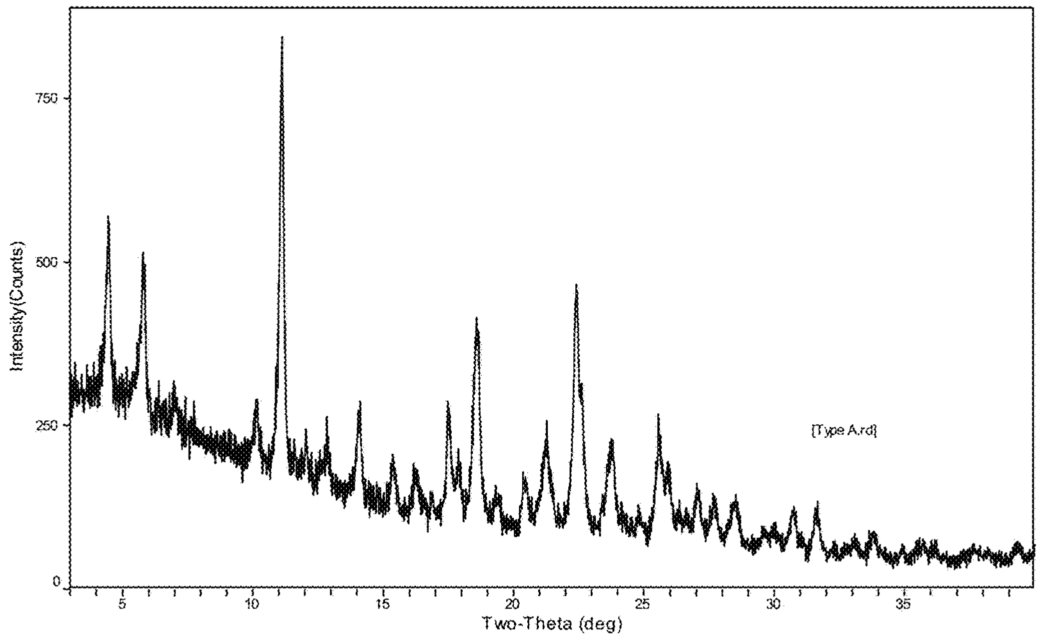
FIG. 9. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 5.
Figure 10:
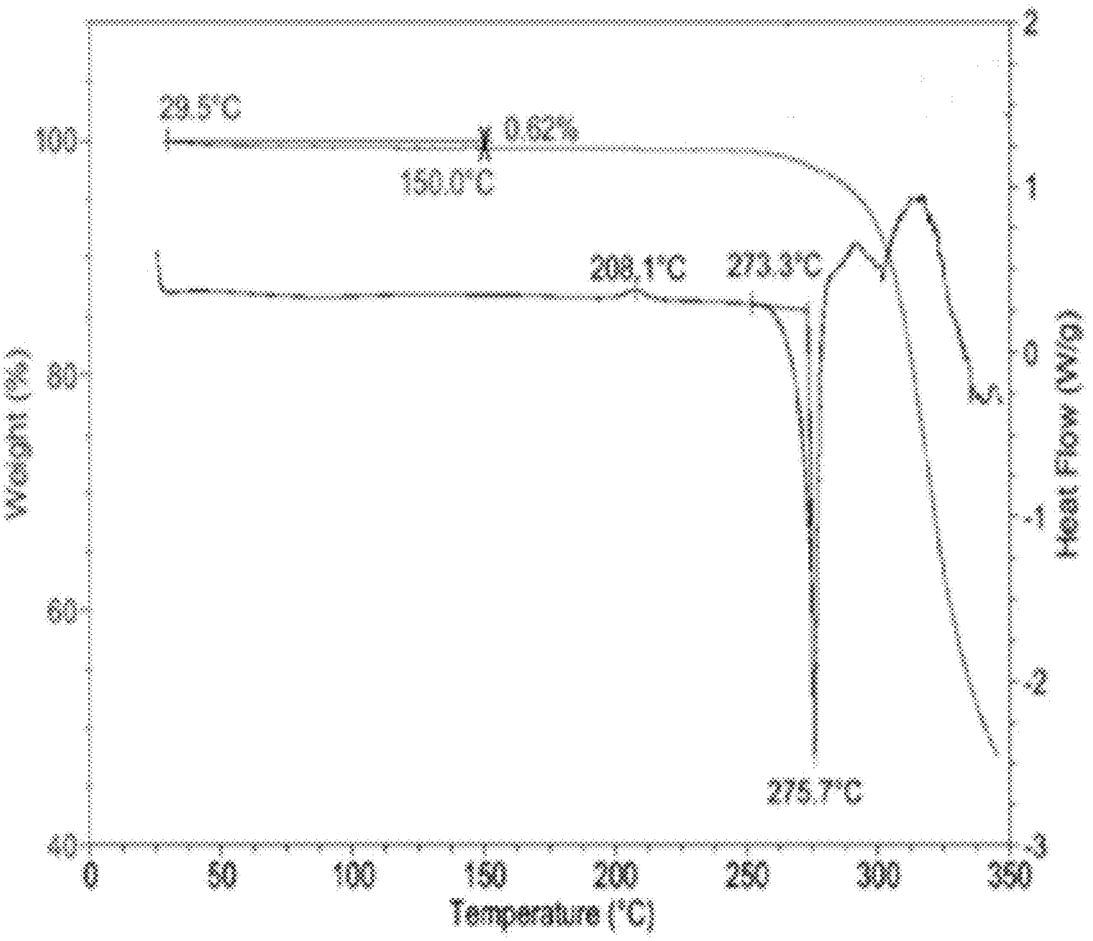
FIG. 10. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 5.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 5 characterized as having at least one of the following properties:

(a) an X-ray powder diffraction (XRPD) pattern substantially the same as shown in FIG. 9;

(b) an X-ray powder diffraction (XRPD) pattern with characteristic peaks at 4.4° 2-Theta, 5.8° 2-Theta, 11.1° 2-Theta, 14.1° 2-Theta, 17.5° 2-Theta, 18.6° 2-Theta, 21.3° 2-Theta, 22.4° 2-Theta, 23.8° 2-Theta, 25.6° 2-Theta, and 25.9° 2-Theta;

(c) a thermogravimetric analysis (TGA) substantially similar to the one set forth in FIG. 10;

(d) a DSC thermogram substantially similar to the one set forth in FIG. 10;

(e) a DSC thermogram with an endotherm having an onset at about 273° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, has an X-ray powder diffraction (XRPD) pattern substantially the same as shown in FIG. 9. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, has an X-ray powder diffraction (XRPD) pattern with characteristic peaks at 4.4° 2-Theta, 5.8° 2-Theta, 11.1° 2-Theta, 14.1° 2-Theta, 17.5° 2-Theta, 18.6° 2-Theta, 21.3° 2-Theta, 22.4° 2-Theta, 23.8° 2-Theta, 25.6° 2-Theta, and 25.9° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, has a thermogravimetric analysis (TGA) thermogram substantially similar to the one set forth in FIG. 10. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, has a DSC thermogram substantially similar to the one set forth in FIG. 10. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, has a DSC thermogram with an endotherm having an onset at about 273° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is obtained from DMSO/water. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 5, is unsolvated.

Crystalline Compound 1, Form 6

Figure 11:
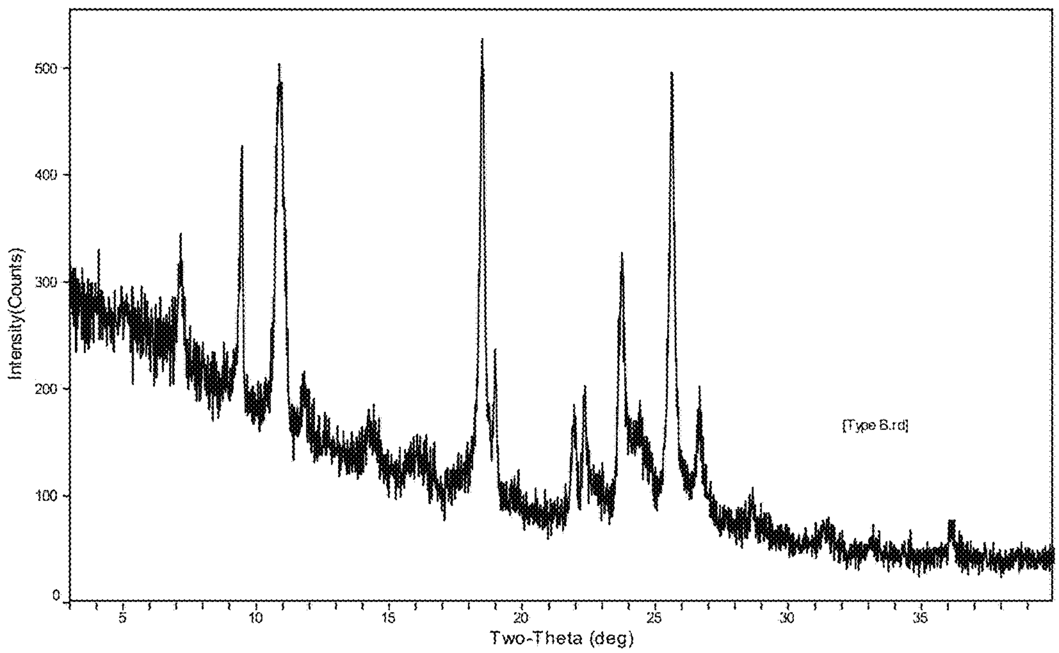
FIG. 11. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 6.
Figure 12:
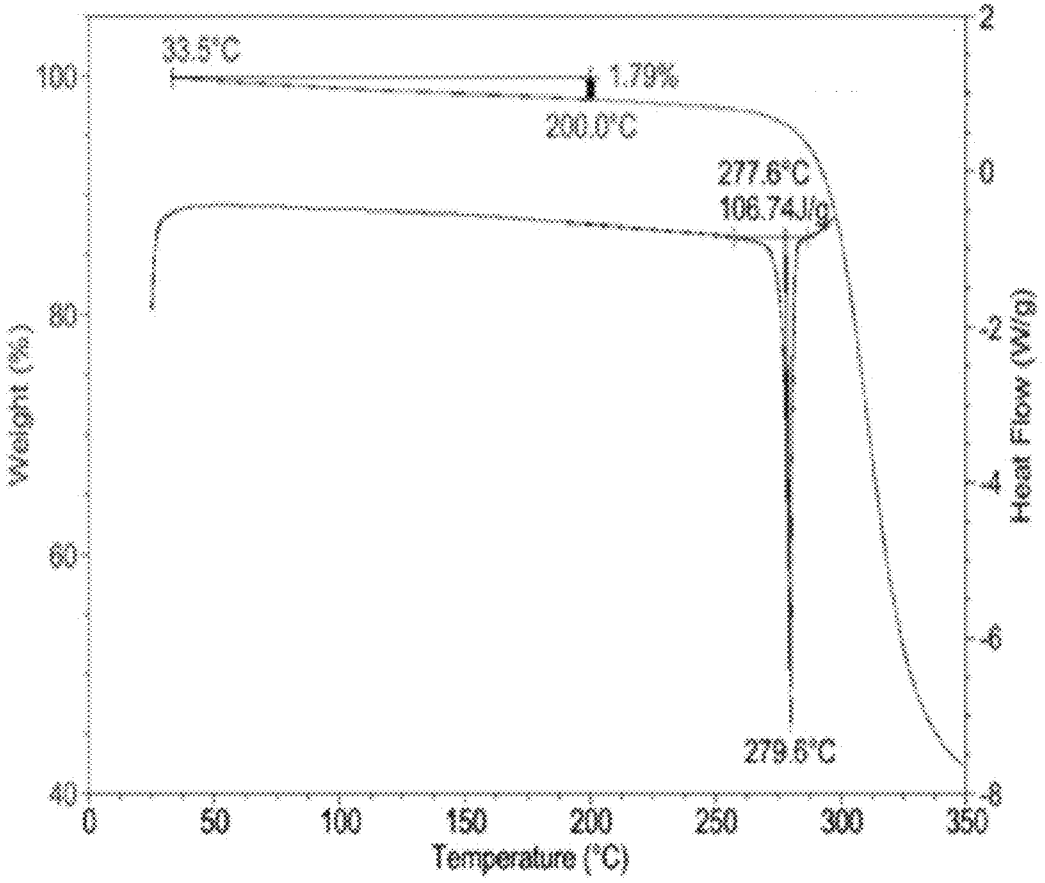
FIG. 12. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 6.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 6 characterized as having at least one of the following properties:

(a) an X-ray powder diffraction (XRPD) pattern substantially the same as shown in FIG. 11;

(b) an X-ray powder diffraction (XRPD) pattern with characteristic peaks at 7.2° 2-Theta, 9.5° 2-Theta, 10.9° 2-Theta, 18.5° 2-Theta, 19.0° 2-Theta, 21.9° 2-Theta, 22.4° 2-Theta, 23.7° 2-Theta, 25.6° 2-Theta, and 26.7° 2-Theta;

(c) a thermogravimetric analysis (TGA) substantially similar to the one set forth in FIG. 12;

(d) a DSC thermogram substantially similar to the one set forth in FIG. 12;

(e) a DSC thermogram with an endotherm having an onset at about 278° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, has an X-ray powder diffraction (XRPD) pattern substantially the same as shown in FIG. 11. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, has an X-ray powder diffraction (XRPD) pattern with characteristic peaks at 7.2° 2-Theta, 9.5° 2-Theta, 10.9° 2-Theta, 18.5° 2-Theta, 19.0° 2-Theta, 21.9° 2-Theta, 22.4° 2-Theta, 23.7° 2-Theta, 25.6° 2-Theta, and 26.7° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, has a thermogravimetric analysis (TGA) thermogram substantially similar to the one set forth in FIG. 12. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, has a DSC thermogram substantially similar to the one set forth in FIG. 12. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, has a DSC thermogram with an endotherm having an onset at about 278° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is obtained from dichloromethane/methanol/heptane. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 6, is unsolvated.

Crystalline Compound 1, Form 7

Figure 13:
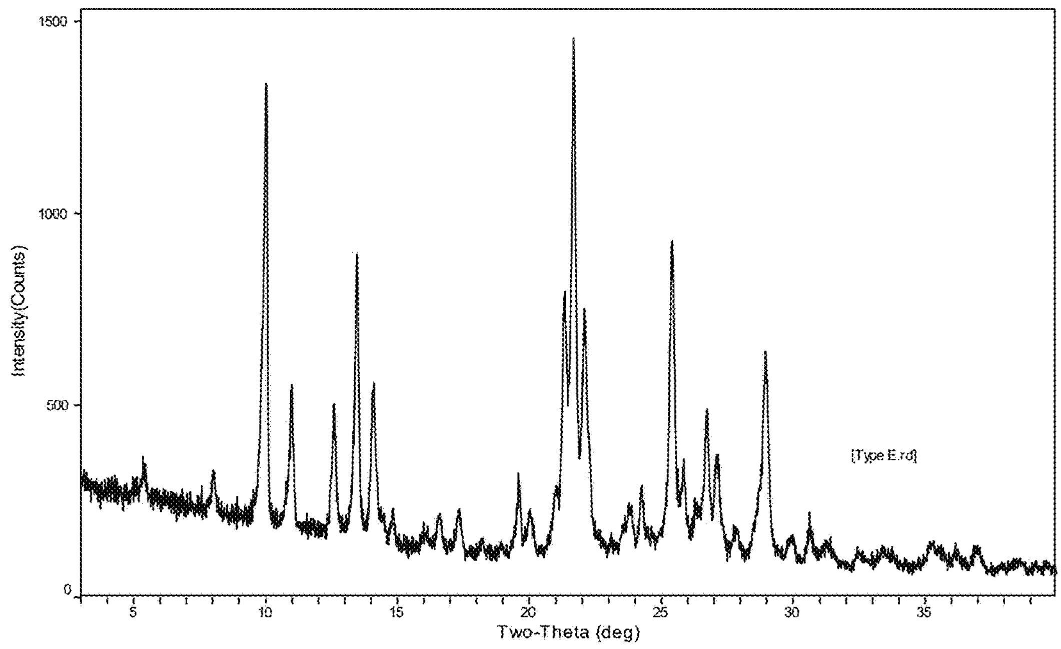
FIG. 13. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 7.
Figure 14:
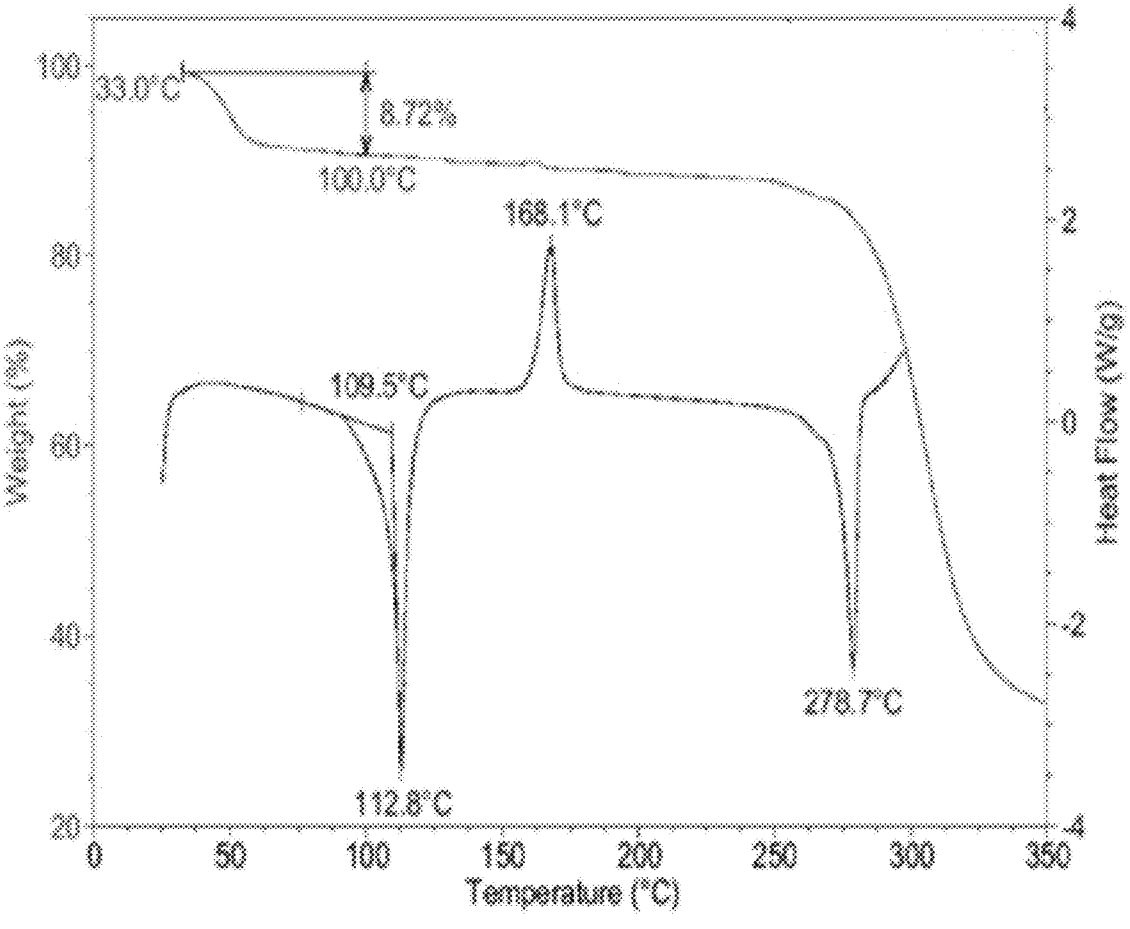
FIG. 14. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 7.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 7 characterized as having at least one of the following properties:

(a) an X-ray powder diffraction (XRPD) pattern substantially the same as shown in FIG. 13;

(b) an X-ray powder diffraction (XRPD) pattern with characteristic peaks at 10.0° 2-Theta, 11.0° 2-Theta, 12.6° 2-Theta, 13.5° 2-Theta, 14.1° 2-Theta, 21.3° 2-Theta, 21.7° 2-Theta, 22.1° 2-Theta, 25.4° 2-Theta, 26.7° 2-Theta, 27.1° 2-Theta, and 29.0° 2-Theta;

(c) a thermogravimetric analysis (TGA) substantially similar to the one set forth in FIG. 14;

(d) a DSC thermogram substantially similar to the one set forth in FIG. 14;

(e) a DSC thermogram with a first endotherm at about 113° C., an exotherm at about 168° C., and a second endotherm at about 279° C.; or (f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, has an X-ray powder diffraction (XRPD) pattern substantially the same as shown in FIG. 13. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, has an X-ray powder diffraction (XRPD) pattern with characteristic peaks at 10.0° 2-Theta, 11.0° 2-Theta, 12.6° 2-Theta, 13.5° 2-Theta, 14.1° 2-Theta, 21.3° 2-Theta, 21.7° 2-Theta, 22.1° 2-Theta, 25.4° 2-Theta, 26.7° 2-Theta, 27.1° 2-Theta, and 29.0° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, has a thermogravimetric analysis (TGA) thermogram substantially similar to the one set forth in FIG. 14. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, has a DSC thermogram substantially similar to the one set forth in FIG. 14. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, has a DSC thermogram with a first endotherm at about 113° C., an exotherm at about 168° C., and a second endotherm at about 279° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is obtained from methanol/water. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is a hydrate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 7, is unsolvated.

Crystalline Compound 1, Form 8

Figure 15:
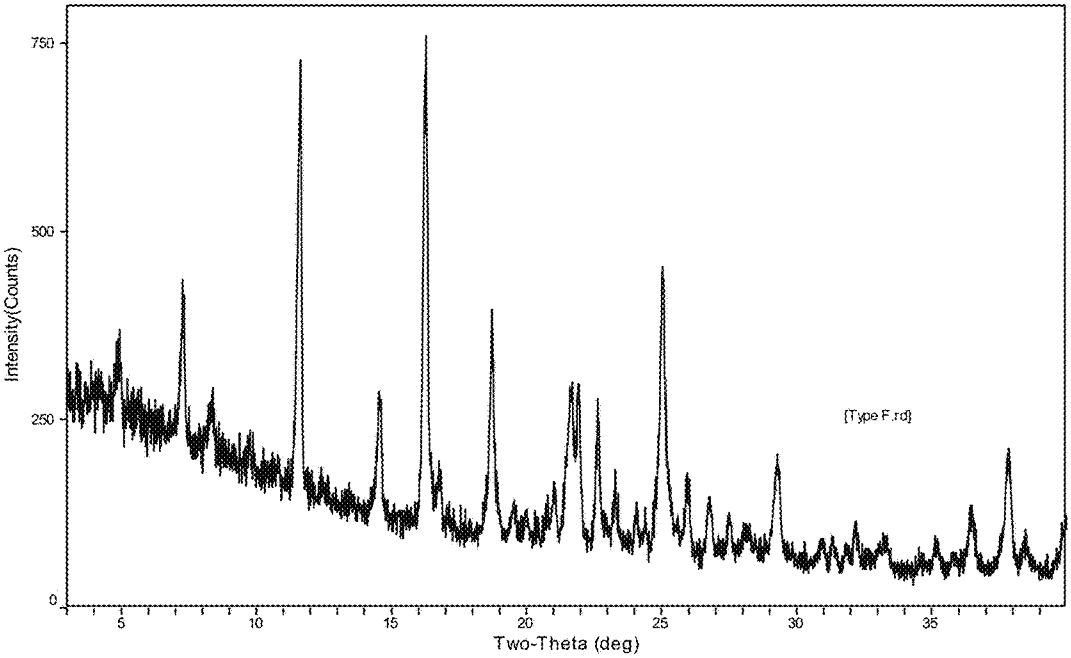
FIG. 15. Illustrates an X-ray powder diffraction (XRPD) pattern of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 8.
Figure 16:
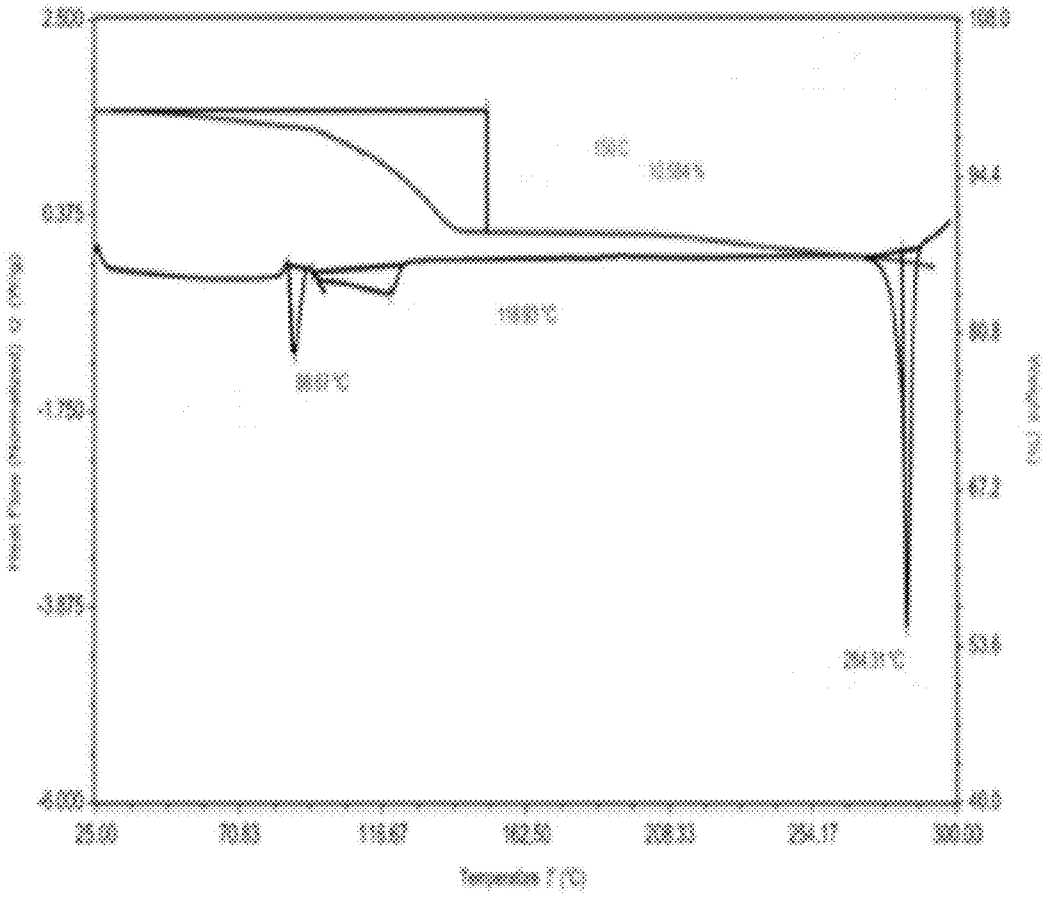
FIG. 16. Illustrates a thermogravimetric analysis (TGA) and differential scanning calorimetry (DSC) thermogram of crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 8.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is Form 8 characterized as having at least one of the following properties:

(a) an X-ray powder diffraction (XRPD) pattern substantially the same as shown in FIG. 15;
(b) an X-ray powder diffraction (XRPD) pattern with characteristic peaks at 7.3° 2-Theta, 11.6° 2-Theta, 14.6° 2-Theta, 16.3° 2-Theta, 18.7° 2-Theta, 21.7° 2-Theta, 21.9° 2-Theta, 22.6° 2-Theta, 25.1° 2-Theta, 29.3° 2-Theta, and 37.8° 2-Theta;
(c) a thermogravimetric analysis (TGA) substantially similar to the one set forth in FIG. 16;
(d) a DSC thermogram substantially similar to the one set forth in FIG. 16;
(e) a DSC thermogram with a first endotherm at about 89° C., a second endotherm at about 119° C., and a third endotherm at about 284° C.; or
(f) combinations thereof.

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is characterized as having at least two of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is characterized as having at least three of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is characterized as having at least four of the properties selected from (a) to (e). In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is characterized as having properties (a) to (e).

In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, has an X-ray powder diffraction (XRPD) pattern substantially the same as shown in FIG. 15. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, has an X-ray powder diffraction (XRPD) pattern with characteristic peaks at 7.3° 2-Theta, 11.6° 2-Theta, 14.6° 2-Theta, 16.3° 2-Theta, 18.7° 2-Theta, 21.7° 2-Theta, 21.9° 2-Theta, 22.6° 2-Theta, 25.1° 2-Theta, 29.3° 2-Theta, and 37.8° 2-Theta. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, has a thermogravimetric analysis (TGA) thermogram substantially similar to the one set forth in FIG. 16. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, has a DSC thermogram substantially similar to the one set forth in FIG. 16. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, has a DSC thermogram with a first endotherm at about 89° C., a second endotherm at about 119° C., and a third endotherm at about 284° C. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is obtained from DMSO/water. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is solvated. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is a DMSO solvate. In some embodiments, crystalline (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, Form 8, is unsolvated.

Preparation of Crystalline Compound 1

In some embodiments, Compound 1 is prepared as described in US2019/0241556, which is herein incorporated by reference in its entirety. In some embodiments, crystalline forms of Compound 1 are prepared as outlined in the Examples. It is noted that solvents, temperatures and other reaction conditions presented herein may vary.

In certain embodiments, provided herein are methods for making a solid form of Compound 1, comprising 1) obtaining a saturated solution of Compound 1 in a solvent at a first temperature (e.g., about 50° C.); 2) adding an anti-solvent into the saturated solution at the first temperature; 3) cooling down to a second temperature (e.g., about −5° C. to room temperature); and 4) collecting a solid if there is precipitation, and evaporating the solvent to collect a solid if there is no precipitation; and 5) optionally drying. In certain embodiments, provided herein are methods for making a solid form of Compound 1, comprising 1) obtaining a saturated solution of Compound 1 in a solvent at about 50° C.; 2) adding an anti-solvent into the saturated solution at about 50° C.; 3) cooling down to about room temperature; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the ratio by volume of solvent and anti-solvent is about 1:4.

In certain embodiments, the ratio by volume of solvent and anti-solvent is about 1:2. In certain embodiments, the ratio by volume of solvent and anti-solvent is about 1:1. In certain embodiments, the methods for making a solid form of Compound 1 are anti-solvent recrystallization experiments.

In another embodiment, crystalline Compound 1, Form 1, is substantially pure. In certain embodiments, the substantially pure crystalline Compound 1, Form 1, is substantially free of other solid forms, e.g., amorphous solid. In certain embodiments, the purity of the substantially pure crystalline Compound 1, Form 1, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 2, is substantially pure. In certain embodiments, the substantially pure crystalline Compound 1, Form 2, is substantially free of other solid forms, e.g., amorphous solid. In certain embodiments, the purity of the substantially pure crystalline Compound 1, Form 2, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 3, is substantially pure. In certain embodiments, the substantially pure crystalline Compound 1, Form 3, is substantially free of other solid forms, e.g., amorphous solid. In certain embodiments, the purity of the substantially pure crystalline Compound 1, Form 3, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 4, is substantially pure. In certain embodiments, the substantially pure crystalline Compound 1, Form 4, is substantially free of other solid forms, e.g., amorphous solid. In certain embodiments, the purity of the substantially pure crystalline Compound 1, Form 4, is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene.

Class 3 solvents, which possess low toxicity, include: acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1 comprise an organic solvent(s). In some embodiments, compositions comprising Compound 1 comprise a residual amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine. In some embodiments, the Class 3 solvent is selected from the group consisting of acetone, ethyl acetate, isopropyl acetate, tert-butyl methyl ether, heptane, isopropanol, and ethanol.

In some embodiments, compositions comprising Compound 1 comprise a residual amount of a Class 2 solvent. In some embodiments, the organic solvent is a Class 2 solvent. In some embodiments, the Class 2 solvent is selected from the group consisting of acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene. In some embodiments, the Class 2 solvent is selected from the group consisting of acetonitrile, tetrahydrofuran, and toluene. In some embodiments, the Class 2 solvent is acetonitrile.

In some embodiments, compositions comprising Compound 1 comprise a residual amount of a solvent for which no adequate toxicological data were found. In some embodiments, the organic solvent is a solvent for which no adequate toxicological data were found. In some embodiments, the solvent is selected from the group consisting of 2-butanone and 2-methyltetrahydrofuran.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1 is absorbed into the general circulation when the pharmaceutical composition is taken orally as compared to intravenous injection.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1 may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. As an example, one can determine such prophylactically effective amounts by a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, $IC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1) with other chemical components, such as carriers, stabilizers, diluents, dispersing agents, suspending agents, thickening agents, and/or excipients. The pharmaceutical composition facilitates administration of the compound to a mammal. In practicing the methods of treatment or use provided herein, therapeutically effective amounts of Compound 1 are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In some embodiments is a pharmaceutical composition comprising (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), and a pharmaceutically acceptable excipient. In some embodiments is a pharmaceutical composition comprising a crystalline form of Compound 1, and a pharmaceutically acceptable excipient. In some embodiments is a pharmaceutical composition comprising a crystalline form of Compound 1, Form 1, and a pharmaceutically acceptable excipient. In some embodiments is a pharmaceutical composition comprising a crystalline form of Compound 1, Form 2, and a pharmaceutically acceptable excipient. In some embodiments is a pharmaceutical composition comprising a crystalline form of Compound 1 tosylate, Form 3, and a pharmaceutically acceptable excipient. In some embodiments is a pharmaceutical composition comprising a crystalline form of Compound 1 mesylate, Form 4, and a pharmaceutically acceptable excipient. In some embodiments is a pharmaceutical composition comprising a crystalline form of Compound 1, Form 5, and a pharmaceutically acceptable excipient. In some embodiments is a pharmaceutical composition comprising a crystalline form of Compound 1, Form 6, and a pharmaceutically acceptable excipient. In some embodiments is a pharmaceutical composition comprising a crystalline form of Compound 1, Form 7, and a pharmaceutically acceptable excipient. In some embodiments is a pharmaceutical composition comprising a crystalline form of Compound 1, Form 8, and a pharmaceutically acceptable excipient.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, and a co-agent, are both administered to a patient simultaneously in the form of a single entity or dosage. The term "non-fixed combination" means that the active ingredients, e.g. Compound 1, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal, or transdermal administration routes. As used herein, the term "subject" or "individual" is used to mean an animal, preferably a mammal, including a human or non-human. The terms individual, patient and subject may be used interchangeably.

Moreover, the pharmaceutical compositions described herein, which include Compound 1 can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of Compound 1 with one or more pharmaceutical excipients to form a bulk blend composition. When referring to these bulk blend compositions as homogeneous, it is meant that the particles of Compound 1 are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include Compound 1, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences,* 20th Edition (2000), a film coating is provided around the formulation of Compound 1. In one embodiment, some or all of the particles of the Compound 1 are coated. In another embodiment, some or all of the particles of the Compound 1 are microencapsulated. In still another embodiment, the particles of the Compound 1 are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol, and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the Compound 1 from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as calcium, magnesium, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non water-soluble diluent" represents compounds typically used in the formulation of pharmaceuticals, such as calcium phosphate, calcium sulfate, starches, modified starches, microcrystalline cellulose, microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition.

Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of Compound 1 from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of Compound 1 inside of a capsule. In some embodiments, the formulations (non-aqueous suspensions and solutions) are placed in a soft gelatin capsule. In some embodiments, the formulations (non-aqueous suspensions and solutions) are placed in a hard shell gelatin capsule.

In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1 and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with Compound 1 which sufficiently isolate the Compound 1 from other non-compatible excipients. Materials compatible with Compound 1 are those that delay the release of the compounds of Compound 1 in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated Compound 1 may be formulated by several methods, illustrative examples of which include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound 1 are microencapsulated prior to being formulated into one of the above forms. In still another embodiment, some or most of the particles are coated prior to being further formulated by using standard coating procedures, such as those described in Remington's Pharmaceutical Sciences, 20th Edition (2000).

In other embodiments, the solid dosage formulations of the Compound 1 are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound 1 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract.

In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in the stomach and dissolve in the intestine;

Cellulose Derivatives. Examples of suitable cellulose derivatives are ethyl cellulose; and reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 m. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, or HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include Compound 1 are delivered using a pulsatile dosage form. A pulsatile dosage form is capable of providing one or more immediate release pulses at predetermined time points after a controlled lag time or at specific sites. Other types of controlled release systems may be used. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al.,

*Pharmaceutical Dosage Forms,* 2 Ed., Vol. 1, pp. 209-214 (1990); Singh et al., *Encyclopedia of Pharmaceutical Technology,* $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of Compound 1 and at least one dispersing agent or suspending agent for oral administration to a subject. The formulations may be a powder and/or granules for suspension and, upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Methods

In another aspect is a method of treating a disease, disorder or condition in a mammal that would benefit from SiP receptor modulation comprising administering to the mammal a therapeutically effective amount of a crystalline form of Compound 1 described herein.

In another embodiment is a method of treating a disease, disorder or condition in a mammal that would benefit from SiP receptor modulation comprising administering to the mammal a therapeutically effective amount of a crystalline form of Compound 1 described herein; wherein the disease, disorder or condition in a mammal is selected from multiple sclerosis, ulcerative colitis, and Crohn's disease. In another embodiment is a method of treating a disease, disorder or condition in a mammal that would benefit from SiP receptor modulation comprising administering to the mammal a therapeutically effective amount of a crystalline form of Compound 1 described herein; wherein the disease, disorder or condition in a mammal is multiple sclerosis. In another embodiment is a method of treating a disease, disorder or condition in a mammal that would benefit from SiP receptor modulation comprising administering to the mammal a therapeutically effective amount of a crystalline form of Compound 1 described herein; wherein the disease, disorder or condition in a mammal is ulcerative colitis. In another embodiment is a method of treating a disease, disorder or condition in a mammal that would benefit from SiP receptor modulation comprising administering to the mammal a therapeutically effective amount of a crystalline form of Compound 1 described herein; wherein the disease, disorder or condition in a mammal is Crohn's disease.

In a further embodiment is a method of treating a disease, disorder or condition in a mammal that would benefit from SiP receptor modulation comprising administering to the mammal a therapeutically effective amount of a crystalline form of Compound 1 described herein; wherein the disease, disorder or condition in a mammal is rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

Methods of Dosing and Treatment Regimens

In some embodiments, crystalline Compound 1 is used in the preparation of medicaments for the treatment of diseases or conditions that would benefit from SiP receptor modulation. In addition, a method for treating any of the diseases or conditions described herein in an individual in need of such treatment, involves administration of pharmaceutical compositions containing crystalline Compound 1, or pharmaceutically acceptable solvate thereof, in therapeutically effective amounts to said individual.

In some embodiments, compositions containing crystalline Compound 1 are administered for prophylactic, therapeutic, or maintenance treatment. In some embodiments, compositions containing Compound 1 are administered for therapeutic applications. In some embodiments, compositions containing Compound 1 are administered for prophylactic applications.

In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder, or condition, previous therapy, the patient's health status and response to the drugs, and the judgment of the treating physician.

In some embodiments, crystalline Compound 1 is administered daily. In some embodiments, crystalline Compound 1 is administered every other day.

In some embodiments, crystalline Compound 1 is administered once per day. In some embodiments, crystalline Compound 1 is administered twice per day. In some embodiments, crystalline Compound 1 is administered three times per day. In some embodiments, crystalline Compound 1 is administered four times per day.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered, if necessary. Subsequently, the dosage or the frequency of administration, or both, can be reduced, as a function of the symptoms, to a level at which the improved disease, disorder, or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein.

Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In some embodiments, compositions include a compound described herein formulated in a compatible pharmaceutical carrier are prepared, placed in an appropriate container, and labeled for treatment of an indicated condition.

For example, the container(s) include crystalline Compound 1, as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

List of Abbreviations

As used throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
eq or equiv equivalent(s)
Et ethyl
$Et_2O$ diethyl ether
EtOH ethanol
EtOAc ethyl acetate
HPLC high performance liquid chromatography
Me methyl
MeOH methanol
MS mass spectroscopy
GC gas chromatography
h hour(s)
KF Karl Fischer
min minutes
MsOH methanesulfonic acid
NMR nuclear magnetic resonance
RP-HPLC reverse phase-high performance liquid chromatography
RT or rt room temperature
TFA trifluoroacetic acid
THE tetrahydrofuran
TLC thin layer chromatography
V volumes

I. Synthesis of Polymorphs

Example 1: Compound 1, Form 1

20 mg of Compound 1 and 0.3 mL of solvent (THF or EtOAc) were stirred at RT for three days and the resulting solids were isolated and dried at 50° C. for 2 h to provide Compound 1, Form 1.

Example 2: Compound 1, Form 2

200 mg of Compound 1 and 2 mL of acetic acid in a vial were stirred at RT for 2 h. Solids were isolated and dried at RT for overnight to provide Compound 1, Form 2.

Scale-up synthesis of Compound 1, Form 2:

1) Charged DMAc (6 V) to a reactor at 25±5° C. under $N_2$.
2) Charged Compound 1 (1.0 eq.) to the reactor at 25±5° C. under $N_2$.
3) Charged DMAc (1 V) to rinse the reactor at 25±5° C. under $N_2$.
4) Adjusted temperature to 110±5° C. and stirred for at least 24 h.
5) Adjusted temperature to 25±5° C.
6) Charged $H_2O$ (7 V) to the reactor at least 5 h at 30±10° C., stirred for at least 4 h.
7) Filtered and washed the wet cake with $H_2O$ (2 V) twice.
8) Dried cake for at least 20 h at 60±5° C.
9) Charged AcOH (8 V) to the reactor at 25±5° C. under $N_2$.
10) Charged the dried cake to the reactor at 25±5° C. under $N_2$.
11) Charged AcOH (2 V) to rinse the reactor at 25±5° C. under $N_2$.
12) Adjusted temperature to 95±5° C.
13) Stirred for 1 h at 95±5° C.
14) Adjusted temperature to 55±5° C.
15) Filtered through activated charcoal (50 wt %).
16) Washed the activated charcoal with AcOH (2 V) twice.
17) Concentrated the filtrate to 5-6 V at no more than 60° C.
18) Charged n-heptane (18 V) to the reactor in at least 6 h at 55±5° C. and stirred for at least 1 h.
19) Adjusted temperature to 25±5° C. and stirred for at least 12 h.
20) Filtered and washed the wet cake with heptane (5.0 V) twice.
21) Dried the cake and purged with nitrogen for no more than 1 hour.
22) Sampled for XRPD and confirmed Form 2.

Example 3: Compound 1 Tosylate, Form 3

20 mg of Compound 1 and 0.3 mL of EtOAc were added into a vial, followed by adding para-toluenesulfonic acid with a molar charge ratio of 1:1 (acid/base). The mixtures were stirred at RT for three days and the resulting solids were isolated and dried at 50° C. for 2 h to provide Compound 1 tosylate, Form 3.

Example 4: Compound 1 Mesylate, Form 4

20 mg of Compound 1 and 0.3 mL of EtOAc were added into a vial, followed by adding methanesulfonic acid with a molar charge ratio of 1:1 (acid/base). The mixtures were stirred at RT for three days and the resulting solids were isolated and dried at 50° C. for 2 h to provide Compound 1, Form 4.

Example 5: Compound 1, Form 5

120 mg of Compound 1 was dissolved in DMSO (4 mL) at 50° C. and then 4 mL of solution was filtered at RT. The filtrate was added with 8 mL water (anti-solvent) over 2 h. Solid precipitated out was collected and dried at 50° C. for 4 h to provide Compound 1, Form 5.

Example 6: Compound 1, Form 6

100 mg of Compound 1 was added to MTBE (2 mL) and the suspension was slurried at rt for 5 h. Solids were isolated to provide Compound 1, Form 6.

Example 7: Compound 1, Form 7

100 mg of Compound 1 was added to 2 mL MeOH/water (v/v, 9/1). The suspension was slurried at RT for 5 h. Solids were isolated to provide Compound 1, Form 7.

Example 8: Compound 1, Form 8

120 mg of Compound 1 was dissolved in DMSO (4 mL) at room temperature for 1 h and the resulting solids were isolated and dried to provide Compound 1, Form 8.

II. Characterization of Polymorphs

Example 9: X-Ray Powder Diffraction (XRPD)

X-ray powder diffraction studies were performed using a Malvern Panalytical Empyrean with the following instrument parameters:

Scan: 3° (2θ) to 40° (2θ)
Increment: 0.0167° (2θ)
Scan speed: 17.8 sec/step
Voltage: 45 KV
Current: 40 mA
Rotation: On
Sample hold: Zero-background sample holder XRPD analysis of Form 1 of Compound 1 (FIG. 1) showed Form 1 to be crystalline with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta.

XRPD analysis of Form 2 of Compound 1 (FIG. 3) showed Form 2 to be crystalline with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta.

XRPD analysis of Form 3 of Compound 1 (FIG. 5) showed Form 3 to be crystalline with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta.

XRPD analysis of Form 4 of Compound 1 (FIG. 7) showed Form 4 to be crystalline with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta.

XRPD analysis of Form 5 of Compound 1 (FIG. 9) showed Form 5 to be crystalline with characteristic peaks at 4.4° 2-Theta, 5.8° 2-Theta, 11.1° 2-Theta, 14.1° 2-Theta, 17.5° 2-Theta, 18.6° 2-Theta, 21.3° 2-Theta, 22.4° 2-Theta, 23.8° 2-Theta, 25.6° 2-Theta, and 25.9° 2-Theta.

XRPD analysis of Form 6 of Compound 1 (FIG. 11) showed Form 6 to be crystalline with characteristic peaks at 7.2° 2-Theta, 9.5° 2-Theta, 10.9° 2-Theta, 18.5° 2-Theta, 19.0° 2-Theta, 21.9° 2-Theta, 22.4° 2-Theta, 23.7° 2-Theta, 25.6° 2-Theta, and 26.7° 2-Theta.

XRPD analysis of Form 7 of Compound 1 (FIG. 13) showed Form 7 to be crystalline with characteristic peaks at 10.0° 2-Theta, 11.0° 2-Theta, 12.6° 2-Theta, 13.5° 2-Theta, 14.1° 2-Theta, 21.3° 2-Theta, 21.7° 2-Theta, 22.1° 2-Theta, 25.4° 2-Theta, 26.7° 2-Theta, 27.1° 2-Theta, and 29.0° 2-Theta.

XRPD analysis of Form 8 of Compound 1 (FIG. 15) showed Form 8 to be crystalline with characteristic peaks at 7.3° 2-Theta, 11.6° 2-Theta, 14.6° 2-Theta, 16.3° 2-Theta, 18.7° 2-Theta, 21.7° 2-Theta, 21.9° 2-Theta, 22.6° 2-Theta, 25.1° 2-Theta, 29.3° 2-Theta, and 37.8° 2-Theta.

Example 10: Thermogravimetric Analysis

Thermogravimetric analysis of solid was performed using TA Q500/Q5000 from TA Instruments. The sample was placed in an open aluminum pan, the amount was weighed automatically. The sample was heated at the heating rate of 10° C./min up to the final temperature.

TGA of Form 1 of Compound 1 (FIG. 2) showed 1.3% weight loss prior to 150° C. consistent with an anhydrate.

TGA of Form 2 of Compound 1 (FIG. 4) showed 9.0% weight loss prior to 150° C. consistent with a mono-acetic acid solvate.

TGA of Form 3 of Compound 1 (FIG. 6) showed 2.4% weight loss prior to 150° C. consistent with an anhydrate.

TGA of Form 4 of Compound 1 (FIG. 8) showed 4.3% weight loss prior to 130° C.

TGA of Form 5 of Compound 1 (FIG. 10) showed 0.6% weight loss up to 150° C. consistent with an anhydrate.

TGA of Form 6 of Compound 1 (FIG. 12) showed 1.8% weight loss up to 200° C. consistent with an anhydrate.

TGA of Form 7 of Compound 1 (FIG. 14) showed 8.7% weight loss up to 100° C. consistent with a hydrate.

TGA of Form 8 of Compound 1 (FIG. 16) showed 10.6% weight loss up to 150° C.

Example 11: Differential Scanning Calorimetry (DSC)

DSC studies were performed using a TA Q200/Q2000 from TA Instruments. The sample was weighed in pinhole aluminum pan and the accurate amount was recorded. The sample was heated at the heating rate of 10° C./min with 50 mL/min nitrogen purge from 25° C. up to the final temperature.

DSC analysis of Form 1 of Compound 1 (FIG. 2) showed a sharp melting endotherm with onset at 282° C.

DSC analysis of Form 2 of Compound 1 (FIG. 4) showed a first endotherm having an onset at about 145° C. and a second endotherm having an onset at about 280° C.

DSC analysis of Form 3 of Compound 1 (FIG. 6) showed a first endotherm at about 41° C., a second endotherm having an onset at about 93° C., and a third endotherm having an onset at about 156° C.

DSC analysis of Form 4 of Compound 1 (FIG. 8) showed a first endotherm at about 60° C. and a second endotherm having an onset at about 128° C.

DSC analysis of Form 5 of Compound 1 (FIG. 10) showed an endotherm having an onset at about 273° C.

DSC analysis of Form 6 of Compound 1 (FIG. 12) showed an endotherm having an onset at about 278° C.

DSC analysis of Form 7 of Compound 1 (FIG. 14) showed a first endotherm at about 113° C., an exotherm at about 168° C., and a second endotherm at about 279° C.

DSC analysis of Form 8 of Compound 1 (FIG. 16) showed a first endotherm at about 89° C., a second endotherm at about 119° C., and a third endotherm at about 284° C.

Example 12: Dynamic Vapor Sorption (DVS)

DVS studies were performed using a DVS Intrinsic (SMS, UK). 10 to 20 mg of compound was transferred into the DVS and the weight change recorded with respect to a varying atmospheric humidity at 25° C. using the following parameters:

Drying at 25° C. until dm/dt<±0.002%/min

Min time: 10 min, Max time: 180 min

Equilibrium: 60 min

Cycle: 0, 5, 10, 20, 30, 40, 50, 60, 70, 80, 90, 80, 70, 60, 50, 40, 30, 20, 10, 5, 0

Characterize the sample after the DVS experiment by XRPD

The DVS analysis of Form 1 of Compound 1 showed 0.3% moisture uptake between 0-80% RH. Post-DVS analysis by XRPD showed no change. The material was slightly hygroscopic.

III. Polymorph Screen

Example 13: Slurry Method at 25° C.

About 15 mg of Compound 1 amorphous free base was suspended in 0.5 mL of solvent in a HPLC glass vial. After the suspension was stirred magnetically for 6 days at RT, the remaining solids were isolated for XRPD analysis. Results are shown in Table 1.

TABLE 1

| Solvent 1 | Solvent 2 | Ratio Solv1/Solv2 | XRPD result |
|---|---|---|---|
| EtOH | — | — | Form 6 |
| acetone | — | — | Form 1 |
| EtOAc | — | — | Form 6 |
| MTBE | — | — | Form 6 |
| THF | — | — | Form 1 |
| 2-MeTHF | — | — | Form 6 |
| ACN | — | — | Form 1 |
| DCM | — | — | Form 1 |
| MeOH | — | — | Form 1 |
| MeOH | water | 93.6/6.4 | Form 1 |
| MeOH | water | 84.4.6/15.6 | Form 7 |
| MeOH | water | 69.6/30.4 | Form 7 |
| MeOH | water | 56.9/43.1 | Form 7 |
| water | — | | Form 5 |

Example 14: Slurry Method at 50° C.

Slurry conversion experiments were conducted at 50° C. in different solvent systems. About 15 mg of Compound 1 amorphous free base was suspended in 0.3 mL of solvent in a HPLC glass vial. After the suspension was stirred for about 6 days at 50° C., the remaining solids were isolated for XRPD analysis. Results are shown in Table 2.

TABLE 2

| Solvent 1 | Solvent 2 | XRPD result |
|---|---|---|
| IPA | — | Form 6 |
| MIBK | — | Form 6 |
| IPAc | — | Form 6 |
| 1,4-dioxane | — | Form 6 |
| ACN | — | Form 1 |
| chloroform | — | Form 6 |
| anisole | — | Form 1 |
| water | — | Form 5 |

Example 15: Solid Vapor Diffusion

Solid vapor diffusion experiments were conducted using 13 different solvents. Approximately 15 mg of Compound 1 free base was weighed into a 3-mL vial, which was placed into a 20-mL vial with 2 mL of volatile solvent. The 20-mL vial was sealed with a cap and kept at RT for 7 days allowing solvent vapor to interact with sample. The solids were tested by XRPD and the results are shown in Table 3.

TABLE 3

| Solvent | XRPD result |
|---|---|
| water | Form 5 |
| MeOH | Forms 1 and 6 |
| IPA | Form 5 |
| acetone | Form 6 |
| EtOAc | Form 6 |
| MTBE | Form 6 |
| THF | Form 6 |
| 1,4-dioxane | Form 6 |
| ACN | Form 1 |
| toluene | Form 1 |
| DCM | Form 6 |
| DMF | Form 1 |
| Acetic acid | Form 2 |

Example 16: Liquid Vapor Diffusion

Nine liquid vapor diffusion experiments were conducted. Approximately 15 mg of Compound 1 free base was dissolved in appropriate solvent to obtain a clear solution in a 3-mL vial. This solution was then placed into a 20-mL vial with 3 mL of volatile solvents. The 20-mL vial was sealed with a cap and kept at RT allowing sufficient time for organic vapor to interact with the solution. The precipitates were isolated for XRPD analysis. The solids were tested by XRPD and the results are shown in Table 4.

TABLE 4

| Solvent | Anti-Solvent | XRPD result |
|---|---|---|
| benzyl alcohol | acetone | Form 1 |
| benzyl alcohol | IPAc | Form 1 |
| benzyl alcohol | ACN | Form 1 |
| DMF | MIBK | Form 1 |
| DMF | IPAc | Form 1 |
| DMF | toluene | Form 1 |
| THF/MeOH (3:1) | toluene | Form 1 |
| THF/MeOH (3:1) | MIBK | Form 1 |
| THF/MeOH (3:1) | heptane | Form 5 |

Example 17: Slow Evaporation

Slow evaporation experiments were performed under six conditions. Briefly, 10-17 mg of Compound 1 free base was dissolved in 2.5 mL of solvent in a 3-mL glass vial. If no dissolution was achieved, suspensions were filtered using a nylon membrane (pore size of 0.45 m) and the filtrates were used for the following steps. The visually clear solutions were covered by Parafilm® with 3-4 pinholes and subjected to evaporation at RT. Results are shown in Table 5.

TABLE 5

| Solvent | XRPD result |
|---|---|
| THF | Form 1 |
| 1,4-dioxane | Form 1 |
| chloroform | Form 6 |
| Acetic Acid | No crystals |
| THF/MeOH (3:1) | Form 1 |
| DCM/MeOH (3:1) | Form 1 |

Example 18: Slow Cooling

Slow cooling experiments were conducted in seven solvent systems. About 20 mg of Compound 1 free base was suspended in 0.5-1.0 mL of solvent in a 3-mL glass vial at RT. The suspension was then heated to 50° C., equilibrated for about five hours and filtered using a nylon membrane (pore size of 0.45 m). Filtrates were slowly cooled down to 5° C. at a rate of 0.1° C./min. No solid was obtained for any system and the solutions were then transferred to −20° C. If no precipitation observed, the solutions were subjected to evaporation at RT. Results are shown in Table 6.

TABLE 6

| Solvent | XRPD result |
|---|---|
| THF | Forms 1 and 6 |
| 1,4-dioxane | Form 6 |
| chloroform | Forms 1 and 6 |
| Benzyl alcohol/MTBE (1:9) | No crystals |
| THF/MeOH (1:1) | Form 1 |
| DCM/MeOH (1:1) | Form 1 |
| DMF/toluene (1:9) | Form 5 |

Example 19: Anti-Solvent Addition

A total of 19 anti-solvent addition experiments were carried out. About 15 mg of Compound 1 free base was dissolved in 0.5-2.0 mL solvent to obtain a clear solution. The solution was magnetically stirred followed by addition of 0.2 mL anti-solvent until precipitate appeared or the total amount of anti-solvent reached 15.0 mL. The obtained precipitate was isolated for XRPD analysis and the results are shown in Table 7.

TABLE 7

| Solvent | Anti-Solvent | XRPD result |
|---|---|---|
| acetic acid | EtOH | Form 1 |
| acetic acid | acetone | Form 1 |
| acetic acid | MTBE | Form 1 |
| acetic acid | water | Form 1 |
| benzyl alcohol | EtOAc | Form 1 |
| benzyl alcohol | MIBK | Form 1 |
| benzyl alcohol | anisole | No solid |
| benzyl alcohol | toluene | Form 1 |
| DMSO | water | Form 5 |
| DMSO | toluene | No solid |
| DMF | IPA | Form 6 |

TABLE 7-continued

| Solvent | Anti-Solvent | XRPD result |
|---|---|---|
| DMF | water | Form 5 |
| DMF | EtOAc | Form 1 |
| THF/MeOH (3:1) | MIBK | Form 1 |
| THF/MeOH (3:1) | ACN | Form 1 |
| THF/MeOH (3:1) | water | Forms 1 and 6 |
| DCM/MeOH (3:1) | IPAc | Form 1 |
| DCM/MeOH (3:1) | Heptane | Form 6 |
| DCM/MeOH (3:1) | 2-MeTHF | No solid |

Example 20: Stability Study

Physicochemical stability was evaluated for Form 1 via storing samples under 80° C. for one day, 25° C./60% RH and 40° C./75% RH for one week and one month. Stability samples were characterized by XRPD and HPLC, with no substantial change in HPLC purity under all tested conditions, indicating good chemical stability. Furthermore, no form change was observed for Form 1 after storage as evidenced by XRPD patterns.

Form 2 stability was also evaluated via slurry in acetone and methanol/water at RT. Solids were isolated at 1 h, 3 h, 5 h and 29 h time points. XRPD analysis showed Form 1 formation in both solvents within one hour.

Example 21: Thermodynamic Stability Relationship of Anhydrates (Forms 1, 5, and 6)

Starting with Form 5, an exothermic signal was observed during the heating with Form 6 formed at elevated temperature. According to the Burger-Ramberger Rules, Form 6 is monotropically related to Form 5 and is thermodynamically more stable.

As a result, slurry competition was performed for Form 6 and Form 1 in acetone and THF systems at 5° C., RT and 50° C. After stirring at desired temperature for five days, the solids were isolated and analyzed by XRPD. As shown in Table 8, only Form 1 was obtained, indicating Form 1 was the thermodynamically stable form from 5-50° C.

TABLE 8

| Solvent | Temperature | XRPD result |
|---|---|---|
| acetone | 5° C. | Form 1 |
| acetone | room | Form 1 |
| acetone | 50° C. | Form 1 |
| THF | 5° C. | Form 1 |
| THF | room | Form 1 |
| THF | 50° C. | Form 1 |

Example 22: Critical Water Activity Study Between Form 1 and Form 7

Critical water activity between anhydrous From 1 and hydrous Form 7 was investigated via slurry in MeOH/$H_2O$ system with various water activities at room temperature. After stirring overnight, the solids were isolated and analyzed by XRPD. As shown in Table 9, Form 7 converted to Form 1 under all water activities at RT, indicating Form 1 is more stable under selected conditions.

TABLE 9

| MeOH/H2O (v:v); $A_w$ | XRPD result |
|---|---|
| 1000:0; 0.0 | Form 1 |
| 937:63; 0.2 | Form 1 |
| 893:107; 0.3 | Form 1 |
| 844:156; 0.4 | Form 1 |
| 775:225; 0.5 | Form 1 |
| 687:313; 0.6 | Form 1 |
| 573:427; 0.7 | Form 1 |
| 418:582; 0.8 | Form 1 |
| 219:781; 0.9 | Form 1 |
| 0:1000; 1.0 | Form 1 |

Example 23: Solubility Evaluation of Form 1 and Form 2

The solubility of Form 1 and Form 2 was evaluated in the same vehicle. Form 1 or Form 2 was added into DCM/MeOH and stirred to dissolve at room temperature or 50° C. A certain amount of HPMC-AS was then added into solution at room temperature, if a clear solution was obtained. The experimental details and results are presented in Table 10. Form 2 dissolved in DCM/MeOH at a concentration of 13 mg/mL, while Form 1 dissolved in a lower concentration, 10 mg/mL. As such, Form 2 showed better solubility than Form 1 in this vehicle and thus is the preferred crystalline form for formulations in this vehicle.

TABLE 10

| Experiment | Input | Quantity (g) | Result |
|---|---|---|---|
| A | DCM | 3.679 | Clear at room |
| | MeOH | 0.752 | temperature |
| | Compound 1, Form 2 | 0.05 | |
| | HPMC-AS | 0.150 | |
| B | DCM | 4.083 | Hazy at 50° C. |
| | MeOH | 0.835 | |
| | Compound 1, Form 1 | 0.05 | |
| | HPMC-AS | 0.166 | |
| C | DCM | 1.633 | Hazy at 50° C. |
| | MeOH | 0.334 | |
| | Compound 1, Form 1 | 0.02 | |
| | AcOH | 0.0022 | |
| | HPMC-AS | 0.0664 | |
| D | DCM | 4.083 | Dissolved at 50° C. |
| | MeOH | 0.834 | Clear at 25° C. after |
| | Compound 1, Form 1 | 0.0414 | stirring for 64 h |
| | HPMC-AS | 0.1378 | |
| E | DCM | 1.633 | Dissolved at 50° C. |
| | MeOH | 0.334 | Clear at 25° C. after |
| | Compound 1, Form 1 | 0.0165 | stirring for 64 h |
| | AcOH | 0.0022 | |
| | HPMC-AS | 0.0549 | |

IV. Single Crystal X-Ray Diffraction Data

Example 24: Single Crystal X-Ray Diffraction, Compound 1. Form 1

A suitable single crystal was selected from the plate-like crystals and analyzed by single-crystal X-ray diffractometer. The crystal system of the single crystal is monoclinic and the space group is P21, the cell parameters are: a=10.70843(9) Å, b=6.96040(5) Å, c=14.85483(12) Å, α=90°, β=100.2303 (8)°, γ=90°, V=1089.602(15) Å3. The formula weight is 546.71 g·mol-1 with Z=2, resulting in the calculated density of 1.666 g·cm-3. Further crystallographic data and the refinement parameters are listed in Table 11.

Figure 17:
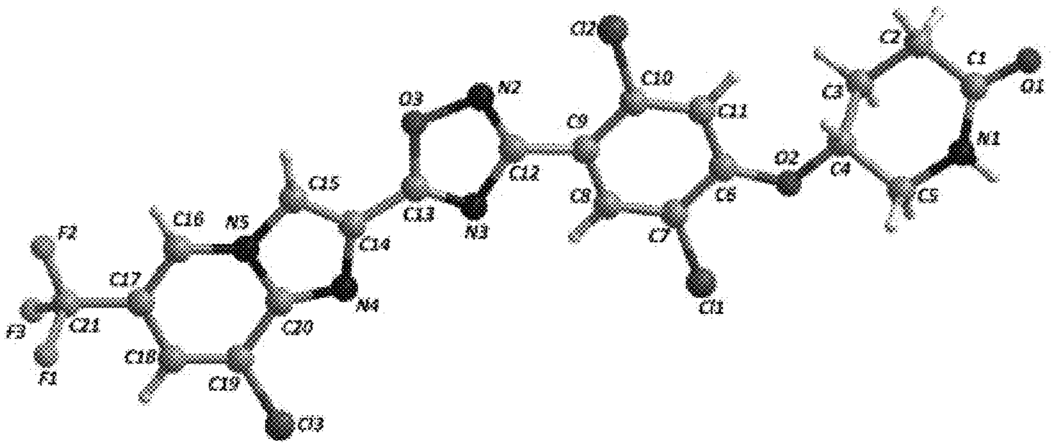
FIG. 17. Illustrates the asymmetric unit in the (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 1 single crystal structure.

The asymmetric unit of the single crystal structure is comprised of only one Compound 1 molecule as shown in FIG. 17, which indicates that the crystal is an anhydrate of Compound 1. The single crystal structure determination confirmed the stereochemistry of Compound 1, which is consistent with the assigned chemical structure. The absolute configuration assignment (R/S) of the chiral atoms in Compound 1 is {C4(R)}. XRPD analysis of the single crystal structure showed it to be Form 1.

TABLE 11

| | |
|---|---|
| Empirical formula | $C_{21}H_{13}Cl_3F_3N_5O_3$ |
| Formula weight (g mol$^{-1}$) | 546.71 |
| Temperature | 120.01(10) K |
| Wavelength (Å) | 1.54184 |
| Crystal system | triclinic |
| Space group | Monoclinic, $P2_1$ |
| Unit cell parameters | |
| a = 10.70843(9)Å | α = 90° |
| b = 6.96040(5) Å | β = 100.2303(8)° |
| c = 14.85483(12) Å | γ = 90° |
| Volume (Å$^3$) | 1089.602(15) |
| Cell formula units, Z | 2 |
| Calculated density (g cm$^{-3}$) | 1.666 |
| Absorption coefficient (mm$^{-1}$) | 4.385 |
| F(000) | 552.0 |
| Crystal size (mm3) | 0.2 × 0.1 × 0.05 |
| 0 range for cell measurement | 6.046 to 152.06 |
| Total reflections collected | 24531 |
| Index ranges | $-13 \leq h \leq 12$; $-8 \leq k \leq 8$; $-18 \leq/\leq 18$ |
| θ range for data collection | $\theta_{min}$ = 3.462°, $\theta_{max}$ = 77.622° |
| Refinement method | full matrix least-squares on $F^2$ |
| Independent reflections | 4435 [$R_{int}$ = 0.0319, $R_\sigma$ = 0.0198] |
| Data/restraints/parameters | 4435/1/317 |
| Goodness-of-fit on $F^2$ | 1.031 |
| Final R indices [ I > 2σ(I) ] | $R_1$ = 0.0225, $wR_2$ = 0.0573 |
| Final R indices [ all data ] | $R_1$ = 0.0244, $wR_2$ = 0.0586 |
| Largest diff. peak and hole (e Å$^{-3}$) | 0.20/−0.21 |
| Flack parameter | −0.010(4) |

Example 25: Single Crystal X-Ray Diffraction, Compound 1. Form 2

Figure 18:
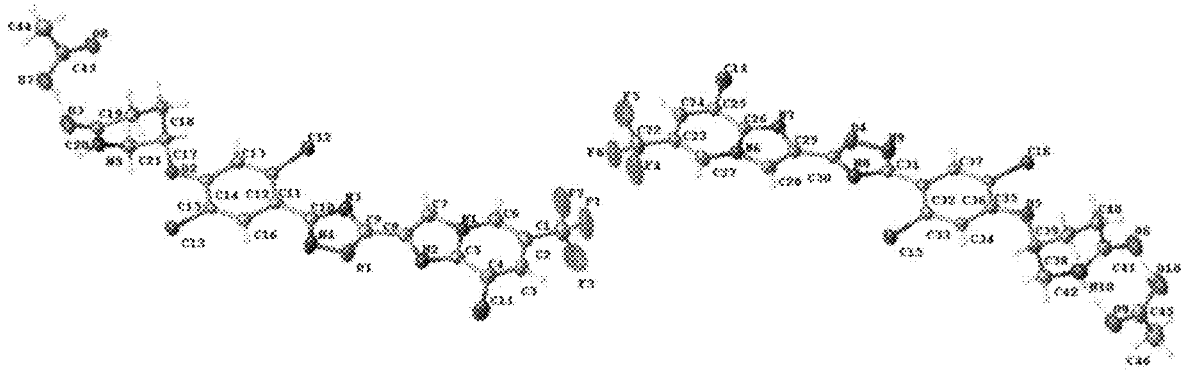
FIG. 18. Illustrates the asymmetric unit in the (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (Compound 1), Form 2 single crystal structure.

Compound 1, Form 2 crystallizes as monoclinic in P21 space group with formula of $C_{21}H_{13}Cl_3F_3N_5O_3{\cdot}C_2H_4O_2$. There are two Compound 1 molecules and two acetic acid molecules in each asymmetric unit, and the unit cell contains two asymmetric units. As shown in FIG. 18, the chiral carbons show "R" (C17, C38) configuration within the asymmetric unit. No proton transfer occurs between Compound 1 and acetic acid, so it is a solvate of acetic acid. Further crystallographic data and the refinement parameters are listed in Table 12. XRPD analysis of the single crystal structure showed it to be Form 2.

TABLE 12

| | |
|---|---|
| Empirical formula | $C_{21}H_{13}Cl_3F_3N_5O_3$ |
| Formula weight (g mol$^{-1}$) | 606.77 |
| Temperature | 180.00(10) K |
| Wavelength (Å) | 1.54184 |
| Crystal system | Monoclinic |
| Space group | $P2_1$ |

TABLE 12-continued

| Unit cell parameters | |
|---|---|
| a = 7.1211(3) Å | α = 90° |
| b = 14.8581(4) Å | β = 95.674(4)° |
| c = 23.8661(9) Å | γ = 90° |
| Volume ($Å^3$) | 2512.80(16) |
| Cell formula units, Z | 4 |
| Calculated density (g $cm^{-3}$) | 1.604 |
| Absorption coefficient ($mm^{-1}$) | 0.434 |
| F(000) | 1232.0 |
| Crystal size ($mm^3$) | 0.61 × 0.05 × 0.02 |
| Total reflections collected | 61505 |
| Index ranges | −9 ≤ h ≤ 10; −20 ≤ k ≤ 19; −34 ≤/≤ 33 |
| 2θ range for data collection | $\theta_{min}$ = 5.146°, $\theta_{max}$ = 61.506° |
| Independent reflections | 13688 [$R_{int}$ = 0.0679, $R_\sigma$ = 0.0619] |
| Data/restraints/parameters | 13668/1/707 |
| Goodness-of-fit on $F^2$ | 1.070 |
| Final R indices [ I > 2σ(I) ] | $R_1$ = 0.0605, $wR_2$ = 0.1236 |
| Final R indices [ all data ] | $R_1$ = 0.0847, $wR_2$ = 0.1316 |
| Largest diff. peak and hole (e $Å^{-3}$) | 0.41/−0.27 |
| Flack parameter | 0.01(3) |

V. Biological Data

Example 26: GTPγS Binding Assay

S1P1 membrane is prepared from CHO-Ki Gαqi5 cells expression full-length human S1P1. Scintillation proximity assay (SPA) is performed by incubating membranes, GTP$\gamma^{35}$S, and compounds at various concentrations for 60 minutes. Wheat germ agglutinin-coated SPA beads are added and incubated for 60 minutes before centrifugation and scintillation counting. $EC_{50}$ data for Compound 1 found to be <1 μM.

We claim:

1. A crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, wherein the crystalline form is Form 1 having at least one of the following properties:

(a) an X-ray powder diffraction (XRPD) pattern substantially the same as shown in FIG. 1;

(b) an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta;

(c) a thermo-gravimetric analysis (TGA) substantially similar to the one set forth in FIG. 2;

(d) a DSC thermogram substantially similar to the one set forth in FIG. 2;

(e) a DSC thermogram with an endotherm having an onset at about 282° C.; or (f) combinations thereof.

2. The crystalline form of claim 1, wherein the crystalline form has an X-ray powder diffraction (XRPD) pattern substantially the same as shown in FIG. 1.

3. The crystalline form of claim 1, wherein the crystalline form has an X-ray powder diffraction (XRPD) pattern with characteristic peaks at 16.5° 2-Theta, 18.5° 2-Theta, 21.0° 2-Theta, 22.1° 2-Theta, 22.8° 2-Theta, 26.6° 2-Theta, 27.8° 2-Theta, and 28.9° 2-Theta.

4. The crystalline form of claim 1, wherein the crystalline form has a thermo-gravimetric analysis (TGA) substantially similar to the one set forth in FIG. 2.

5. The crystalline form of claim 1, wherein the crystalline form has a DSC thermogram substantially similar to the one set forth in FIG. 2.

6. The crystalline form of claim 1, wherein the crystalline form has a DSC thermogram with an endotherm having an onset at about 282° C.

7. The crystalline form of claim 1, wherein the crystalline form is characterized as having properties (a), (b), (c), (d), and (e).

8. A crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one, wherein the crystalline form is Form 2 having at least one of the following properties:

(a) an X-ray powder diffraction (XRPD) pattern substantially the same as shown in FIG. 3;

(b) an X-ray powder diffraction (XRPD) pattern with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta;

(c) a thermo-gravimetric analysis (TGA) substantially similar to the one set forth in FIG. 4;

(d) a DSC thermogram substantially similar to the one set forth in FIG. 4;

(e) a DSC thermogram with a first endotherm having an onset at about 145° C. and a second endotherm having an onset at about 280° C.; or (f) combinations thereof.

9. The crystalline form of claim 8, wherein the crystalline form has an X-ray powder diffraction (XRPD) pattern substantially the same as shown in FIG. 3.

10. The crystalline form of claim 8, wherein the crystalline form has an X-ray powder diffraction (XRPD) pattern with characteristic peaks at 6.9° 2-Theta, 17.1° 2-Theta, 18.1° 2-Theta, 22.0° 2-Theta, 24.0° 2-Theta, 24.8° 2-Theta, 25.5° 2-Theta, 26.2° 2-Theta, and 28.2° 2-Theta.

11. The crystalline form of claim 8, wherein the crystalline form has a thermo-gravimetric analysis (TGA) substantially similar to the one set forth in FIG. 4.

12. The crystalline form of claim 8, wherein the crystalline form has a DSC thermogram substantially similar to the one set forth in FIG. 4.

13. The crystalline form of claim 8, wherein the crystalline form has a DSC thermogram with a first endotherm having an onset at about 145° C. and a second endotherm having an onset at about 280° C.

14. The crystalline form of claim 8, wherein the crystalline form is characterized as having properties (a), (b), (c), (d), and (e).

15. A crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one para-toluenesulfonic acid salt, wherein the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one para-toluenesulfonic acid salt is Form 3 having at least one of the following properties:

(a) an X-ray powder diffraction (XRPD) pattern substantially the same as shown in FIG. 5;

(b) an X-ray powder diffraction (XRPD) pattern with characteristic peaks at 4.9° 2-Theta, 8.4° 2-Theta, 17.5° 2-Theta, 19.8° 2-Theta, 20.5° 2-Theta, 24.8° 2-Theta, 25.6° 2-Theta, and 26.4° 2-Theta;

(c) a thermo-gravimetric analysis (TGA) substantially similar to the one set forth in FIG. 6;

(d) a DSC thermogram substantially similar to the one set forth in FIG. 6;

(e) a DSC thermogram with a first endotherm at about 41° C., a second endotherm having an onset at about 93° C., and a third endotherm having an onset at about 156° C.; or (f) combinations thereof.

16. A crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one is a methanesulfonic acid salt, wherein the crystalline form of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one methanesulfonic acid salt is Form 4 having at least one of the following properties:

(a) an X-ray powder diffraction (XRPD) pattern substantially the same as shown in FIG. 7;

(b) an X-ray powder diffraction (XRPD) pattern with characteristic peaks at 10.8° 2-Theta, 15.4° 2-Theta, 17.3° 2-Theta, 18.2° 2-Theta, 19.2° 2-Theta, 20.1° 2-Theta, 21.6° 2-Theta, 22.8° 2-Theta, 23.4° 2-Theta, 24.8° 2-Theta, 25.3° 2-Theta, 26.7° 2-Theta, and 30.9° 2-Theta;

(c) a thermo-gravimetric analysis (TGA) substantially similar to the one set forth in FIG. 8;

(d) a DSC thermogram substantially similar to the one set forth in FIG. 8;

(e) a DSC thermogram with a first endotherm at about 60° C. and a second endotherm having an onset at about 128° C.; or (f) combinations thereof.

17. A pharmaceutical composition comprising the crystalline form of claim 1, and a pharmaceutically acceptable excipient.

18. A method of treating a disease, disorder or condition in a mammal that would benefit from sphingosine-1-phosphate (SIP) receptor modulation, comprising administering to the individual a therapeutically effective amount of a crystalline form of claim 1, wherein the disease, disorder or condition in a mammal is selected from multiple sclerosis, ulcerative colitis, and Crohn's disease.

19. A pharmaceutical composition comprising the crystalline form of claim 8, and a pharmaceutically acceptable excipient.

20. A method of treating a disease, disorder or condition in a mammal that would benefit from sphingosine-1-phosphate (S1P) receptor modulation, comprising administering to the individual a therapeutically effective amount of a crystalline form of claim 8, wherein the disease, disorder or condition in a mammal is selected from multiple sclerosis, ulcerative colitis, and Crohn's disease.

* * * * *